US005960085A

United States Patent [19]
de la Huerga

[11] Patent Number: 5,960,085
[45] Date of Patent: Sep. 28, 1999

[54] SECURITY BADGE FOR AUTOMATED ACCESS CONTROL AND SECURE DATA GATHERING

[76] Inventor: Carlos de la Huerga, 9190 N. Upper River Rd., River Hills, Wis. 53217

[21] Appl. No.: 08/834,634

[22] Filed: Apr. 14, 1997

[51] Int. Cl.$^6$ ............................... H04L 9/32; H04L 9/00; H04L 9/30
[52] U.S. Cl. ..................... 380/25; 380/4; 380/9; 380/23; 380/30; 380/49; 340/825.31; 340/825.34; 340/825.54; 395/186; 395/187.01; 395/188.01; 235/380; 235/382
[58] Field of Search ............................. 380/4, 9, 23, 24, 380/25, 49, 50, 59, 30; 235/379, 380, 382; 395/186, 187.01, 188.01; 340/825.31, 825.34, 825.54; 342/42, 44

[56] References Cited

U.S. PATENT DOCUMENTS

| | | |
|---|---|---|
| 4,384,288 | 5/1983 | Walton ................................ 340/825.34 |
| 4,575,621 | 3/1986 | Dreifus ..................................... 235/380 |
| 4,598,275 | 7/1986 | Ross et al. . |
| 4,730,849 | 3/1988 | Siegal . |
| 4,817,050 | 3/1989 | Komatsu et al. . |
| 4,835,372 | 5/1989 | Gombrich et al. . |
| 4,839,806 | 6/1989 | Goldfischer et al. . |
| 4,850,009 | 7/1989 | Zook et al. . |
| 4,857,713 | 8/1989 | Brown . |
| 4,857,716 | 8/1989 | Gombrich et al. . |
| 4,916,441 | 4/1990 | Gombrich . |
| 5,071,168 | 12/1991 | Shamos . |
| 5,166,498 | 11/1992 | Neeley . |
| 5,193,855 | 3/1993 | Shamos . |
| 5,202,929 | 4/1993 | Lemelson . |
| 5,272,318 | 12/1993 | Gorman . |
| 5,319,711 | 6/1994 | Servi ......................................... 380/23 |
| 5,381,487 | 1/1995 | Shamos . |
| 5,408,655 | 4/1995 | Oren et al. . |
| 5,541,583 | 7/1996 | Mandelbaum ...................... 340/825.54 |
| 5,548,660 | 8/1996 | Lemelson . |
| 5,629,981 | 5/1997 | Nerlikar .................................... 380/25 |

FOREIGN PATENT DOCUMENTS

| | | | |
|---|---|---|---|
| 2154344 | 9/1985 | United Kingdom ..................... 380/25 |

*Primary Examiner*—Bernarr E. Gregory
*Attorney, Agent, or Firm*—Akin, Gump, Strauss, Hauer & Feld, L.L.P.

[57] ABSTRACT

A system utilizing a personal identification badge to collect data and to provide access to a computer terminal. The personal identification badge includes circuitry and transceiver components for transmitting identification information and exchanging other digital information with a computer terminal and other compatible devices. The personal identification badge establishes a wireless communication link with a computer terminal to allow a user to logon to the terminal. When a user leaves the computer terminal, the communication link is terminated, causing the computer terminal to lock the keyboard, blank the monitor, and/or logoff the user if the communication link is not restored within a sufficient time period. The personal identification badge includes means for encrypting and signing digital information. Adapted for use within a hospital, the system provides further means for establishing an affiliation between a personal identification badge and a patient, for collecting digital information from electronic devices that record or gather data regarding the status of a patient, for digitizing and recording dictation spoken into the personal identification badge, and for modifying the digital information so collected to conform to standards, such as those of a Java applet or the hypertext markup language, for interactive display on a universal display browser.

32 Claims, 26 Drawing Sheets

```
<html>
<body>
<a href="http://hww.st._mary.springfield/demographics/987654321/19_May_1996">
ID: 987654321</a><br>
Date: 13:42 19-May-1996<br>
Report type: Medication Dispensing
<br><br>
<table border=2 cellspacing=5>
<tr><td colspan=3 align=center>Medication Given:</td></tr>
<tr><td>Penicillin</td><td>100mg</td><td>2 capsules</td></tr>
<tr><td>Tylenol w/Codeine</td><td>200mg</td><td>1 capsule</td></tr>
</table>
<br>
Dispensed by:
<a href="http://hww.st._mary.springfield/staff_directory/S_W_Johnson.html">
 Sam W. Johnston, R.N.</a>,  at: 13:42 19-May-1996<br>
<br>
ID Device Serial Number: 1265338<br>
</html>
```

Figure 13B

ID: *987654321*
Date 13:59 19_May-1996
Report Type: Medication Administration

| Medication Given: | | |
|---|---|---|
| Penicillin | 100mg | 2 capsules |
| Tylenol w/Codeine | 200mg | 1 capsule |

Dispensed by: *Sam W. Johnston, R.N.*, at: 13:42 19-May-1996

ID Device Serial Number: 1265338

Figure 13C

```
                                                                    440
       <html>

<head>
       <title>Medication Administration</title>
444    </head>

<form action=
       "http://hww.st_mary.springfield/medication/given/987654321/19_May_1996/13:42" method=put>

<a href="http://hww.st._mary.springfield/demographics/987654321/19_May_1996">
       ID: 987654321</a><br>
448
       Report type: Medication Administration<br>
       Patient ID Verified: YES
       <br><br>
452
       <table border=2 cellspacing=5>
       <tr><td colspan=3 align=center>Medication Given:</td></tr>

<tr><td>Penicillin</td><td>100mg</td><td>
       <select name=Penicillin>
       <option>2
       <option>1.5
456    <option>1
       <option>0.5
       <option>none
       </select> capsules</td></tr>

<tr><td>Tylenol w/Codeine</td><td>200mg</td><td>
       <select name=Tylenol_w/Codeine>
       <option>1
460    <option>0.5
       <option>none
       </select> capsule</td></tr>

</table>
       <br>
464
       Given by:
       <a href="http://hww.st._mary.springfield/staff_directory/M_T_Adamson.html">
       Mary T. Adamson, R.N.</a>, at: 13:49 19-May-1996<br>
468
       Dispensed by:
       <a href="http://hww.st._mary.springfield/staff_directory/S_W_Johnson.html">
       Sam W. Johnston, R.N.</a>, at: 13:42 19-May-1996<br>
       <br>
       ID Device Serial Number: 1265338<br>
```

Figure 14A

```
<input type=hidden name=Pat.I.D. value=987654321>
<input type=hidden name=Pat.I.D.Addr
        value="http://hww.st._mary.springfield/demographics/987654321/19_May_1996">
<input type=hidden name=Date value=13:59 19-May-1996>
<input type=hidden name=Report_type value=Medication_Administration>
<input type=hidden name=Patient_ID Verified value=YES>
<input type=hidden name=Med1 value=Penicillin-100mg-2_capsules>
<input type=hidden name=Med2 value=Tylenol_w/Codeine-200mg-1_capsule>
<input type=hidden name=Given_by
value=http://"hww.st._mary.springfield/staff_directory/M_T_Adamson.html"_Mary_T._Adamson,_
R.N-13:49_19-May-1996>
<input type=hidden name=Dispensed_by
value=http://"hww.st._mary.springfield/staff_directory/S_W_Johnson.html"_Sam_W._Johnston,_R.
N.-13:42_19-May-1996>
<input type=hidden name=ID_Device_Serial_Number value=1265338>

<br>
<input type=submit value=Approve&#information>

</html>
```

Figure 14A

ID: *987654321*
Report Type: Medication Administration
Patient ID Verified: YES

Medication Given:

| Penicillin | 100mg | 2 | capsules |
| Tylenol w/Codeine | 200mg | 1 | capsule |

Given by: *Mary T. Adamson, R.N.*, at: 13:49 19-May-1996
Dispensed by: *Sam W. Johnston, R.N.*, at: 13:42 19-May-1996

ID Device Serial Number: 1265338

[ Approve Information ]

Figure 14B

SECURITY BADGE FOR AUTOMATED ACCESS CONTROL AND SECURE DATA GATHERING

FIELD OF THE INVENTION

The present invention relates to computer systems for the management of information distributed across a plurality of intermittently and dynamically linked objects. More particularly, the present invention relates to a system and method for restricting access and monitoring and recording communications between a plurality of system users, a plurality of computer terminals on a computer network, and a plurality of smart devices. Further, the present invention relates to a system for logging a system user onto and off of a computer terminal through means of a device worn by the system user which communicates with the computer terminal.

BACKGROUND OF THE INVENTION

The increasing specialization and complexity of medical care has vastly increased the paperwork and record keeping that must be maintained by doctors, nurses, and other hospital staff persons. This has created an interest in performing routine record keeping, such as that of statistics generated by patient monitoring instruments or of medication dispensed for a patient's care that is typically performed by staff persons, in a more efficient, automatic, and reliable way. The rapid growth of network technologies has also created an interest in using the tools of the Internet to create a hospital Intranet, to link discrete hospital databases and make their data, images, and video records commonly accessible through a remote Internet/Intranet browser. The ease, however, with which electronically stored information may be intercepted and reproduced for illicit purposes has prompted increasing concerns regarding the privacy and authenticity of electronic information. Privacy and authenticity of patient information are particularly important concerns in a hospital.

Gombrich, U.S. Pat. No. 4,916,441 discloses an electronic health care management system using a portable handheld pocket terminal for use by medical staff personnel to upload data from medical instruments and monitoring devices, document and track observations and treatment, display scheduling information, and transmit stored information to the hospital's patient care database. Gombrich et al., U.S. Pat. No. 4,857,716 further discloses the use of barcodes on patient bracelets and patient-specific medical items such as drugs, blood samples, and IVs to be read by a portable handheld pocket terminal with a barcode reader used to provide an audit trail and automatic billing when drugs, therapy, or procedures are administered to patients. However, the pocket terminal of Gombrich is a general-purpose, not user-specific, device and does not automatically enable information exchange. In order to gain access, a caregiver is required to slide a separate card into a separate base unit connected to a base station in order to access the device. Therefore, the pocket terminal is not well-suited as a personal security and identification badge for a particular caregiver. The information gathering capabilities of the Gombrich device are also limited. The Gombrich system contemplates the use of a barcode reading wand to provide access, upload information, and authorize the administration of treatments and use of medical devices. Further, the Gombrich system lacks secure decryption and digital signature means. Even if it were adapted so that the public and private keys of a cryptographic system were encoded upon a user's access card, the user would have to slide the card through the base unit every time a message was to be decoded, encrypted, or digitally signed, or in the alternative, compromise the security of the cryptographic system by uploading the user's public and private key rings onto the pocket terminal.

What is needed is a comprehensive data collection, management, and security system where information that is stored by a variety of hospital devices, such as patient monitors and bedside patient charting systems, would transmit information to an electronic "security badge" worn by a doctor or nurse authorized to care for the patient with whom the hospital device is related. The information exchange would take place automatically when the doctor or nurse came into proximity with the patient and pressed an activation button, and would be downloaded, automatically, to the hospital computer network when the doctor or nurse logged on to a computer terminal.

A data collection and management system further needs means for limiting and monitoring access by a multitude of users to a hospital computer network including a multitude of computer workstations and personal computers. Virtually all data regarding a patient's treatment in a hospital, clinic, or doctor's office is thought to be private. The problem of access control and data security is particularly acute in hospitals. Because hospitals operate around the clock, with multiple shifts and staff persons moving from one floor or one wing of the hospital to another, hospitals are unlikely to assign a computer terminal to a particular user. Further, a hospital presents an almost unique problem of having computer terminals or workstations with sensitive personal data in an unsecured environment. Computer terminals or workstations may be placed in unsupervised patient rooms, conference rooms, or nurse stations. Each such device may be able to retrieve all the records for any patient who has been in the hospital. Standard password protection presents only a small amount of security, as many password choices are easily guessed. If the password is complex users often write their password and leave it near a computer terminal or workstation where others may easily discover the password.

Restricted access systems today range from the simple to the sophisticated. It is typical for multiuser network systems to require a user to log on by entering a name and password to gain access to system information. The user is typically admonished to logout when leaving the workstation environment to prevent unauthorized access. The system may automatically log a user off after a predetermined period of inactivity. For users who must access the system frequently but intermittently, short inactivity periods for automatic logout will be a source of constant inconvenience. Alternatively, if long inactivity periods are used, another user may inadvertently use the terminal under the previous person's security authorization. Moreover, some users may frequently choose obvious or easily ascertainable passwords that can easily be broken. Others may write them down and store them where they may be easily intercepted. While this may not be a significant problem with personal computers in one's home or locked office, stronger and more reliable security is appropriate for sensitive information where computer terminals are shared by many or are located in open locations where others could eavesdrop.

Another restricted access system involves the use of user-specific password-generating devices. Typically, a user seeking access to a secure system is presented a code or instruction on a system terminal screen. The user enters the code or the information demanded by the instruction, via manual entry or optical coupling, into his own password generating device. The password generating device then calculates a second code based upon the user's input and an encryption algorithm stored by the device, and displays this second code to the user for entry into the computer terminal or workstation. After the user enters the second code, the computer terminal or workstation then performs a verification check on it to confirm its creation by the password calculator of an authorized user of the computer terminal or workstation. If confirmed, the user is granted access in accordance with the user's system access privileges.

Yet another restricted access system requires a user to insert an authorization card, e.g. a PCMCIA card, into a computer card reader to authorize access and to authenticate information entered at the computer terminal with the user's digital signature. One potential weakness of such a system is that a hidden program could present documents for signature without the proper control of the user. Another weakness with these implementations is the relatively high risk that an authorized user will forget to or fail to remove his card in the card reader before he leaves the terminal—a risk that is particularly acute for a nurse or doctor who may have to leave a terminal in emergency situations to attend to a patient's care. Also, the loss of the card will result in a significant inconvenience to the owner and the system administrator.

Lemelson, in U.S. Pat. No. 5,202,929 and U.S. Pat. No. 5,548,660, discloses an access control system utilizing detection devices such as speech recognition equipment and fingerprint scanners to analyze one or more physical characteristics of a person attempting access to a computer. The system also incorporates physical presence sensors such as motion detectors and limit switches embedded in seat cushions to track the presence of an authorized user so as to prevent continued access to the system when the authorized user leaves or is absent. This system is primarily directed to accessing desktop computer terminals on a sensitive computer network and is not easily adaptable, however, for restricting access to laptops, portable instruments, medical equipment such as respirators, or electronically-controlled medication dispensers. Moreover, the implementation of the Lemelson invention requires a significant amount of detection equipment and analysis software, which may not be adaptable to the cost, space, and portability requirements of many devices for which restricted access and auditing control is desired.

There is also a need, for purposes of patient protection, quality control, record keeping, billing, and forensics, to monitor, control, and record access to the dispensation and administration of medicine, IVs, blood transfusions, and other treatments as well as the collection, administration, and testing of blood and tissue samples.

Gorman, U.S. Pat. No. 5,272,318 discloses a locked container bearing a barcode which can only be opened by means of a combination that is stored in the memory of a portable barcode scanning device. In order to ascertain this combination, the medical administrator must scan his own administrator code, the barcode on a patient's bracelet, and the barcode on the locked container within a preset time period. If the patient and treatment codes match, the combination is displayed so the administrator may inlock the container and apply the medication stored in the container. However, the access control of the Gorman invention could easily be subverted by writing down the combination that is displayed and opening the container at a later time. As soon as the combination was provided, the inventory sought to be controlled could be tampered with or misappropriated for illegitimate purposes without detection. Also, the container itself is not enablingly disposed with both read and write capabilities. Consequently, it does not perform any record keeping of its own, because the invention as disclosed does not record access, attempted or otherwise, to the container. Better inventory control would be provided if auditing could be performed on the containers themselves as they are returned for recycling. Moreover, an improvement could be made through the use of internal codes such as public and private keys rather than visible barcodes to inhibit attempts to overcome the limited access safeguards of the system.

SUMMARY OF THE INVENTION

The present invention relates to a limited access system for a computer network with a multitude of users. More particularly, the present invention relates to a limited access system providing automatic log-on and log-out for network users by means of coded communications between transceiver devices worn by network users and transceiver devices connected to computer terminals on the network. More particularly, the present invention relates to an automated and secure data gathering and security system for use in a hospital setting.

Many if not most employees and staff members of a hospital are accustomed to wearing an ID badge on their uniform, jacket, or around their neck, as a prerequisite to gaining access to restricted areas and to provide identification to other employees of the hospital. The preferred embodiment of the claimed invention expands the access control function of the basic ID badge by using it to facilitate access control to the hospital computer network and to information generated by various hospital implements such as monitoring devices. It also adds data buffering and wireless communication operability allowing it to gather information from monitoring devices and hospital instruments utilized by the patients receiving the badge-wearer's care. This modified ID badge will hereinafter be described as a "security badge."

In the preferred embodiment, each computer terminal with access to a database on the hospital computer network is equipped with a device for wireless information exchange with the security badge, using infrared transmitters and detectors. To access a computer terminal, a system user (defined as one who is wearing and is authorized to wear a security badge of the preferred embodiment) positions himself in front of the computer terminal so that a generally unobstructed signal path exists between the security badge and the computer terminal. The computer terminal intermittently transmits "interrogation" signals to detect, authenticate, and establish communications with nearby security badges. If a system user is properly positioned, the security badge may capture and process these interrogation signals, returning a signal by which the security verification system of the hospital computer network can authenticate (i.e., identify and verify) the access privileges of the system user. The preferred embodiment utilizes public key cryptography in this identification process.

If the security badge is authenticated through this cryptographic exchange, the system user is automatically logged onto the hospital computer network. The computer terminal displays the system user's own customized startup page through an interactive, hypertext-capable browser interface, and the system user may do anything consistent with the access privileges associated with the security badge. Meanwhile, the computer terminal continues to emit its interrogation signals, so that if the signal path between the security badge and the computer terminal is terminated or obstructed for more than a preset period of time, which could occur, for example, if the system user leaves or turns away from the computer terminal, the screen is blanked off and the keyboard locked, preventing an intruder from gaining access to the computer terminal. If the interruption of the signal path is short-term, the system may restore access to the system user without any change in the display. An interruption lasting longer than a predetermined time period, for example, one minute, may cause the system user to be logged off automatically.

After the user is logged off, the system may be programmed to automatically delete and overwrite any files that have been cached on the computer terminal, disk drive, or RAM memory device during the system user's use. The need for such precautions may be particularly acute with typical Intranet/Internet browser programs that maintain large cache memories and a record of URL's accessed through the browser program. Other steps may be taken to prevent "hackers" from gaining unauthorized access to the computer terminal. For example, after log-off, the terminal may be isolated from remote network access by eliminating any network connection, with the exception of the Security Verification System, to the terminal. The network connection would not be reestablished until the next successful cryptographic exchange between the security badge of a system user and the computer terminal.

In the preferred embodiment, the security badge can be used to perform several other functions relating to data collection and data security. Other devices throughout the hospital may be equipped with transceiver devices capable of communicating patient-related information to the security badge. Such devices may include patient identification wrist bracelets, patient monitors, bedside patient charting systems, patient identification displays, medical instruments, and other hospital implements (more generally referred to as "smart devices"). Communication between such smart devices and a security badge may be enabled when the system user comes into proximity with the smart devices. This would enable information recorded by the system user onto the security badge about the patient to be automatically identified with the appropriate patient for record keeping, reference, and billing purposes. Should, for example, the current readings and settings from a patient monitor, ventilator, or other device be recorded, or a dictation be made about the patient's condition, the information is automatically identified with the patient's identification data provided by the device or a separate device for patient identification. If the hospital uses a system of electronic labeling or smart devices for medication containers or blood or IV bags, any information obtained from these electronic labels or smart devices is identified with the patient.

Standardized formatting and organization of data as it is recorded may also be achieved, so as to reduce the amount of human intervention, and the concomitant risk of error, needed to modify and archive the data for display and storage. In the preferred embodiment, as it receives information via dictation or from hospital implements, the security badge generates a database address for storing the information as a record and formats the record for browser-compatible presentation. Preferably, the information is formatted to a standard consistent with the hypertext markup language (HTML) or with a Java applet that will handle the data. In this manner a user seeking to reference the records at a later time will not be required to locate special programs to present the data, but will be provided full access to the records through a single program such as a typical network browser or through the processing capabilities of a Java enabled processor.

After the security badge has collected and properly formatted data from smart devices, it may transmit the information to a computer terminal onto which it is logged. Moreover, the authenticity of the information transmitted may be guaranteed by having it digitally signed by the security badge prior to transmission.

Another aspect of the present invention provides limited access, via the security badge, to a medical container. This medical container could hold such things as medication, IVs, and blood samples for which an audit trail is desirable. Before a system user can administer treatment, information must be exchanged between the medical container and the security badge authorizing the treatment. The medical container records the patient and system user identification and time of treatment in memory and transmits the patient identification to the security badge. As an extra precaution the security badge may be required to have previously received the patient identification from a patient bracelet or another device having the patient identification and capable of compatible transmission means. This provides for a double audit trail of administered treatment, decreasing the probability of cover-ups for mistreatments or misappropriation of prescription medicine. The recorded information will be transferred to the hospital computer network twice, first when the data records from the security badge are transmitted to the network, and second when the medical container is returned for accounting and recycling.

An object of the claimed invention is to provide a self-authenticating identification badge to provide automatic logon and logout access to a computer system, so as to minimize the number of times a sign-on process is repeated and to minimize the amount of manual input required while maximizing the security of the restricted-access system or device. The present invention transforms the typical hospital identification badge from an implement for identification and access privileges with respect to other individuals to an implement for computerized identification and access privileges.

A more particular object of the claimed invention is to provide a self-authenticating identification badge that remains in frequent communication with a computer device, system, or network to verify the badge wearer's presence. The computer device, system, or network will be programmed to terminate access if this communication is interrupted. This may be implemented through the use of optical, magnetic, electric, radiofrequency, or infrared communications between the badge and a computer system or hospital electronic implement. To access the system, the user wearing the badge must point the badge in the general direction of the transceiver connected with the computer system or hospital electronic implement being accessed. When the user leaves the general vicinity of the computer system or hospital electronic implement, communication between the badge and the computer system or hospital implement is interrupted. During this interruption, the system will go into a lock mode preventing others from accessing, eavesdropping, or intercepting information on or from the system or implement.

Another object of the claimed invention is to reduce the amount of manual data entry, record keeping, and management by providing automated documentation of patient condition, prognosis, and administration of care. A related object of the claimed invention is to minimize the amount of training necessary to implement a comprehensive data collection, data security, and data management system for hospital and patient records. One aspect in which this object is advanced is in the invention's operability to utilize a variety of relatively inexpensive browser applications.

Still another object of the claimed invention is to provide a hospital intranet system to integrate and automate the processes of staff and patient identification, inventory control, comprehensive record keeping and auditing of patient treatment, and data collection and management for analysis, browser-based reference, and storage.

Yet another object of the claimed invention is to provide a portable transceiver and data buffering device for automated information retrieval at the point and time of care. The present invention implements a self-authenticating identification badge providing self-identification to and electronic retrieval of data stored in a variety of hospital electronic implements including diagnostic and monitoring devices and electronic lock-lid containers for medicines, IVs, blood samples, etc.

Still another object of the claimed invention is to provide a portable transceiver and data buffering device incorporating cryptography to prevent intelligible unauthorized interception of transmitted data. This cryptography may also be used to digitally sign and authenticate information that is transmitted by a data transceiver and buffering device to a computer system.

Yet another object of the claimed invention is to provide for easy, browser-based reference of a patient's data records. The present invention provides for automatic formatting of data records as they are created or introduced into or retrieved from the database system. A portable transceiver and data buffering device according to the present invention may generate database addresses for data it records for storage when downloaded to the system. It may also incorporate identification and time stamps into data records stored by the device or the addresses of the data records. Further, the portable transceiver and data buffering device may modify data it records to conform to a standard, such as that of the hypertext markup language (HTML) or a Java applet, amenable for display by a network browser or a Java enabled computer.

Yet another object of the claimed invention is to provide a portable transceiver and data buffering device with a digital dictaphone to digitally record messages for storage with a patient's data records.

Still another object of the claimed invention is to provide a limited access medication dispenser that conditions access on the time of attempted treatment, the identity of the system user attempting to administer the medication disposed within the container, and the identity of the patient for whom the medication was dispensed. The medication dispenser may also record the time and identities of the patient and system user for accounting and billing purposes.

Yet another object of the claimed invention is to provide a hospital intranet system capable of double-auditing in the administration of medicines, IVs, or blood samples disposed within an electronic lock-lid medical container. Both the portable transceiver and data buffering device and the lock-lid medical container would store information about the identity of the nurse or doctor dispensing the treatment, the patient being treated, and the time treatment was given. This double-auditing function provides more thorough inventory control and better protection of patients through better detection of mismanaged care, detection that is not easily subverted by a staff-person's attempts to conceal the treatment.

BRIEF DESCRIPTION OF THE DRAWINGS

The present invention is more easily understood with reference to the drawings, in which:

FIG. 13B is a graphical representation of a medical dispensation record with HTML codes for displaying the information in a network browser.

FIG. 13C is a graphical representation of the record of FIG. 13B as it would be viewed by a system user through a network browser.

FIG. 14A is a graphical representation of a medical administration record with HTML codes for displaying the information in a network browser.

FIG. 14B is a graphical representation of the record of FIG. 14A as it would be viewed by a system user through a network browser.

DETAILED DESCRIPTION OF THE PREFERRED EMBODIMENT

The present invention may be adapted for use in a wide variety of applications, and is suitable for any environment in which numerous data records having one or multiple forms and/or formats are to be collected, stored, archived, retrieved, or translated. By way of illustration and not by way of limitation, the preferred embodiment is presented in the context of a hospital environment, in which typically there are numerous computer systems in use by various health care professionals in one or several hospitals, and each professional often desires to have access to the patient records created by other professionals in that or other hospitals.

Figure 1:
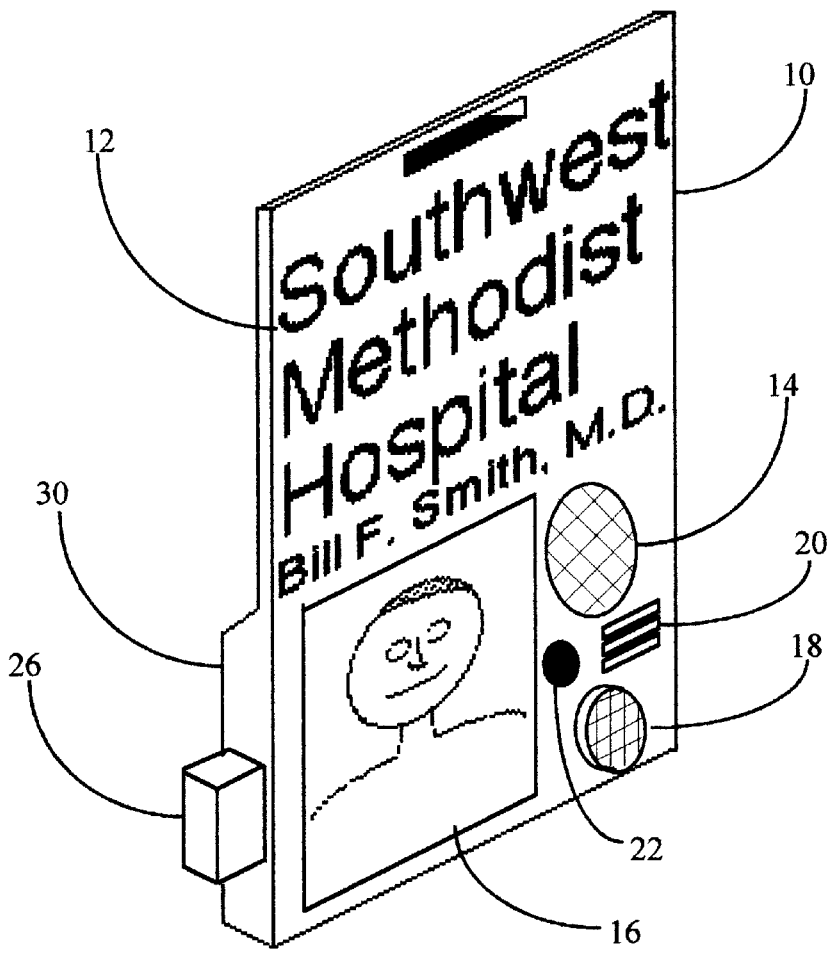
FIG. 1 is a perspective view of a security badge capable of communicating with computer terminals and a plurality of smart devices.

In FIG. 1, the mobile transceiver and data buffering device of the preferred embodiment is illustrated as a security badge 10 which may be clipped to a person's clothing or worn by chain around a person's neck. While this embodiment implements the claimed invention on an ID badge, the claimed invention could be instantiated in other shapes, such as a ring or a personalized pointing device. In keeping with its preferred resemblance to a typical identification badge, the security badge 10 is affixed with identification text 12 and graphic display 16. The security badge 10 incorporates a wireless communication means 14, an audible alerting device 20, an activation button 18, a microphone and digitizer 22, and a dictation button 26. The security badge 10 may also incorporate additional electronic identification means 30, such as a magnetic strip. Because of its low cost, energy efficiency, minimally regulated status, and standardization by the Infrared Data Association (IrDA), infrared transmitter and receiver components (not illustrated) supporting serial infrared communications links are the preferred wireless communication means 14 of the invention. A variety of infrared communications devices, such as Hewlett Packard's HSDL-1001 transceiver components, may be used to implement the preferred communication means. Alternatively, other communication means—such as acoustic, radiofrequency, or electromagnetic coupling—may be supported. The graphic display 16 of the security badge 10 may be any of a variety of forms, including but not limited to a photograph, a light emitting diode array, a liquid crystal panel, and an active-matrix display. Security badge 10 also incorporates processor circuitry 260 illustrated in FIG. 6.

Figure 2:
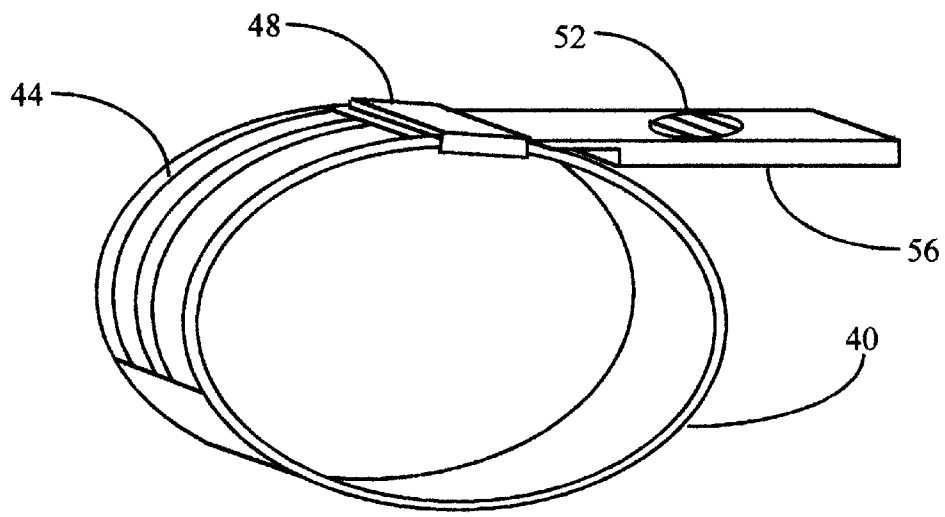
FIG. 2 is a perspective view of a wrist bracelet to be worn by patients or other persons to provide identification through wireless communication with security badges or other smart devices.

In FIG. 2, the wrist bracelet of the preferred embodiment is illustrated as a patient identification bracelet 40 having a flexible, extendible band 44, a securing clasp 48, a processing device 56, and wireless communication means 52. The patient identification bracelet is similar to existing bracelets used to identify patients in hospitals, with the exception of the processing device 56 and communication means 52, which are added. Textual information (not illustrated) is typically affixed to the extendible band 44. Communication means 52 are preferably, but may not be, similar to the wireless communication means 14 of the security badge 10. The processing device 56 of FIG. 2 includes a memory element that contains a variety of patient identification information (see 320, FIG. 9), regarding the patient to whom the wrist bracelet 40 is attached.

Figure 3:
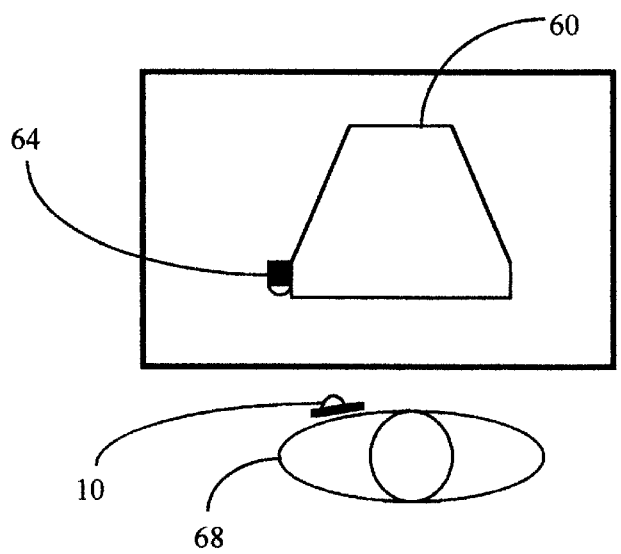
FIG. 3 is a plan view of a computer terminal or workstation being operated by a system user where access is conditioned upon communications between the security badge and the computer terminal.

FIG. 3 graphically illustrates a typical setup that would permit communications between a system user 68 wearing a security badge 10 and a computer terminal 60 equipped with wireless transceiver device 64 compatible with the wireless communication means 14 (FIG. 1) of the security badge 10.

Figure 4:
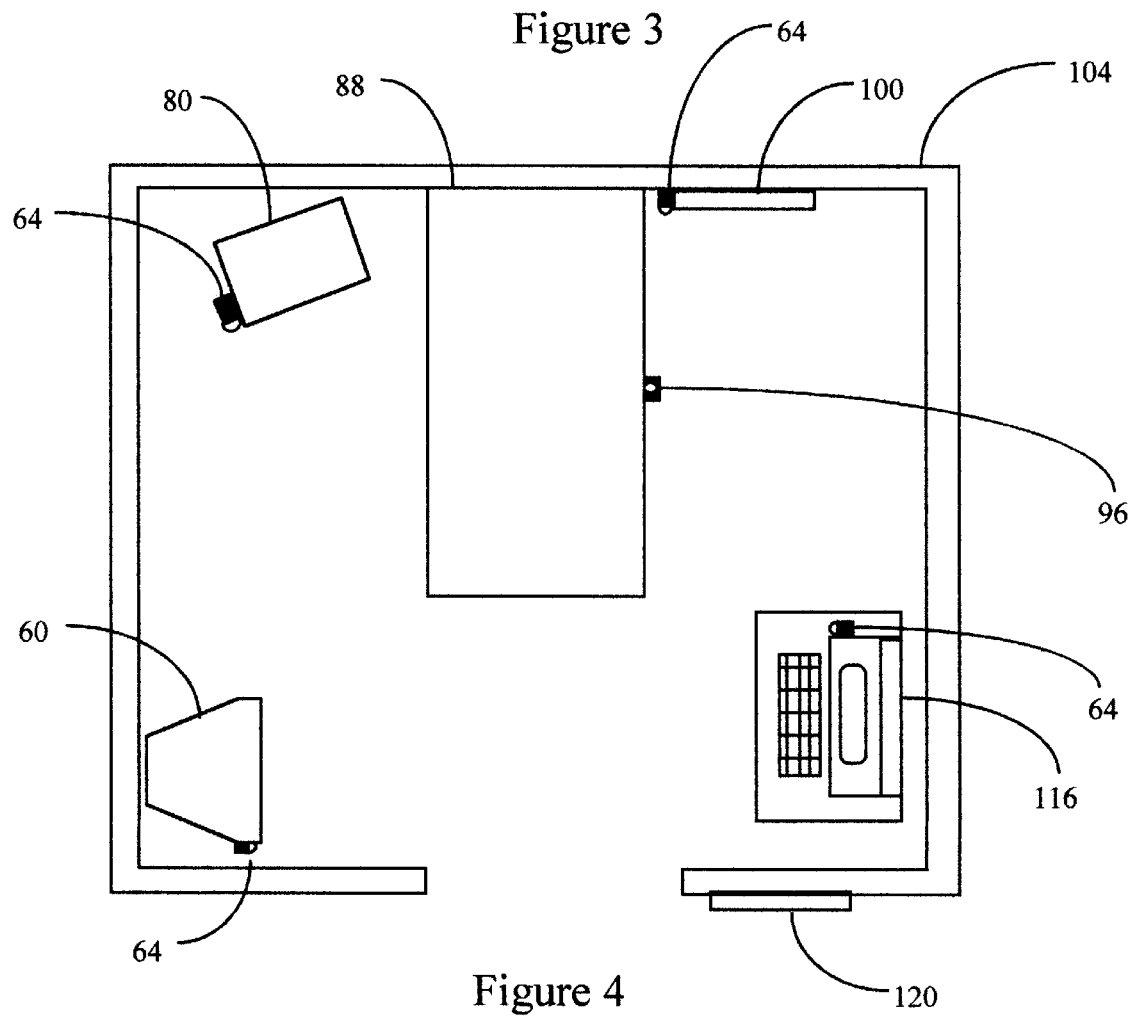
FIG. 4 is a plan view of a hospital patient room equipped with a variety of computerized monitoring, treatment, and information devices.

FIG. 4 sets forth a plan drawing of a patient's room 104 including a computer terminal or workstation 60, a patient monitor 80, and a patient treatment device 116, each equipped with wireless transceiver device 64. Also shown is a patient bed 88 and an optional bedside communication device 96 which may or may not be compatible with wireless transceiver device 64. Communication device 96 may be connected to an optional patient identification display 100 equipped with wireless transceiver device 64 or to a patient identification display 120 outside of the room 104.

Figure 5:
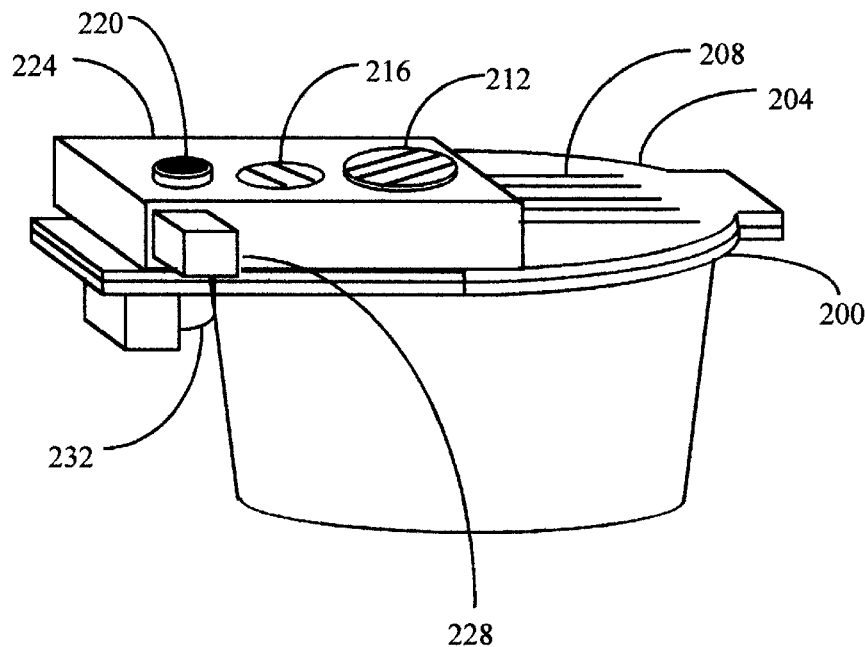
FIG. 5 is a perspective view of a medical container equipped with an electromechanical locking device controlled by communications through transceiver components.

FIG. 5 sets forth a graphical representation of the medical container 200 of the preferred embodiment. Medical container 200, which may be used to transport and provide auditing and limited access for medications, blood or tissue samples, or other inventory, includes a lid 204, a securing latch 232, a latch release button 228, and an electronic identification device 224. Textual identification 208 may be attached to the lid 204. The electronic identification device 224 includes wireless communication means 212 compatible with communication means 14 (FIG. 1) of the security badge 10, and may also include an activation button 220 and an audible alerting device 216. Release of the latch may be conditioned on a time-window for treatment, the successful exchange of identification information between a system user 68's security badge 10 and the electronic identification device 224, and the manual depression of the latch release button 228. The audible alerting device 216 may serve to remind the system user 68 when it is time to apply the enclosed treatment. The electronic identification device 224 further includes means, not illustrated, for storing the medication information structure 340 of FIG. 10.

Figure 6:
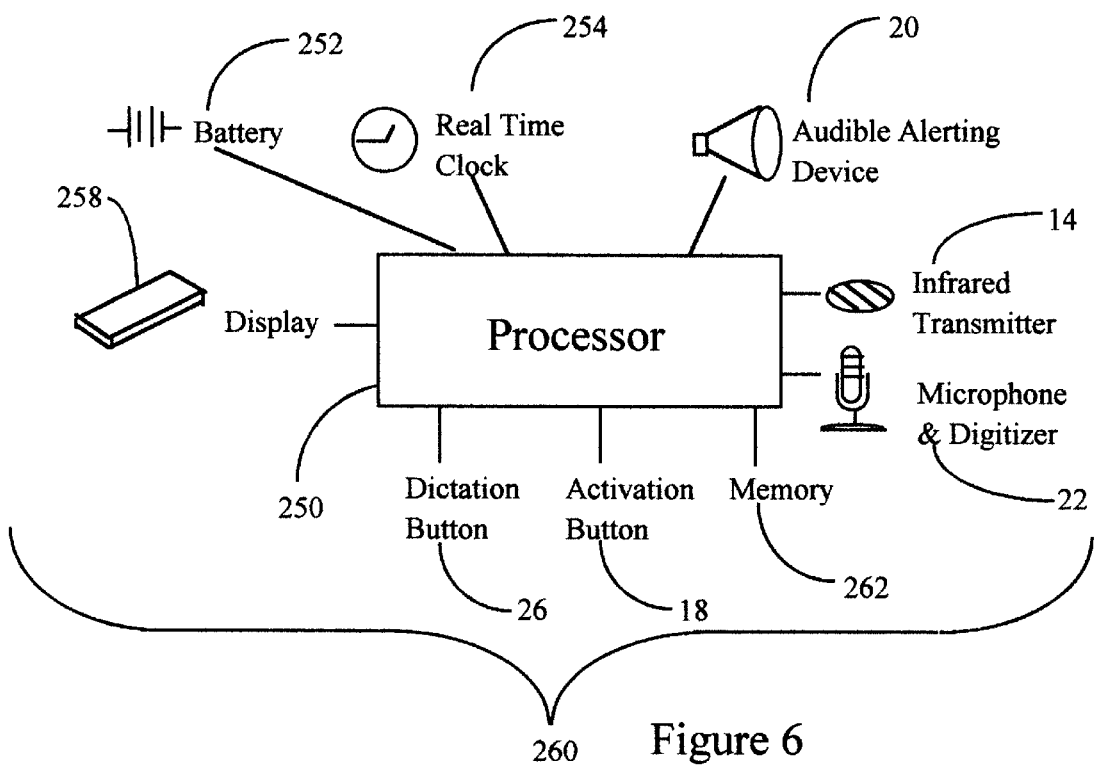
FIG. 6 is a block diagram of various electrical components which may be incorporated within the security badge.
Figure 8:
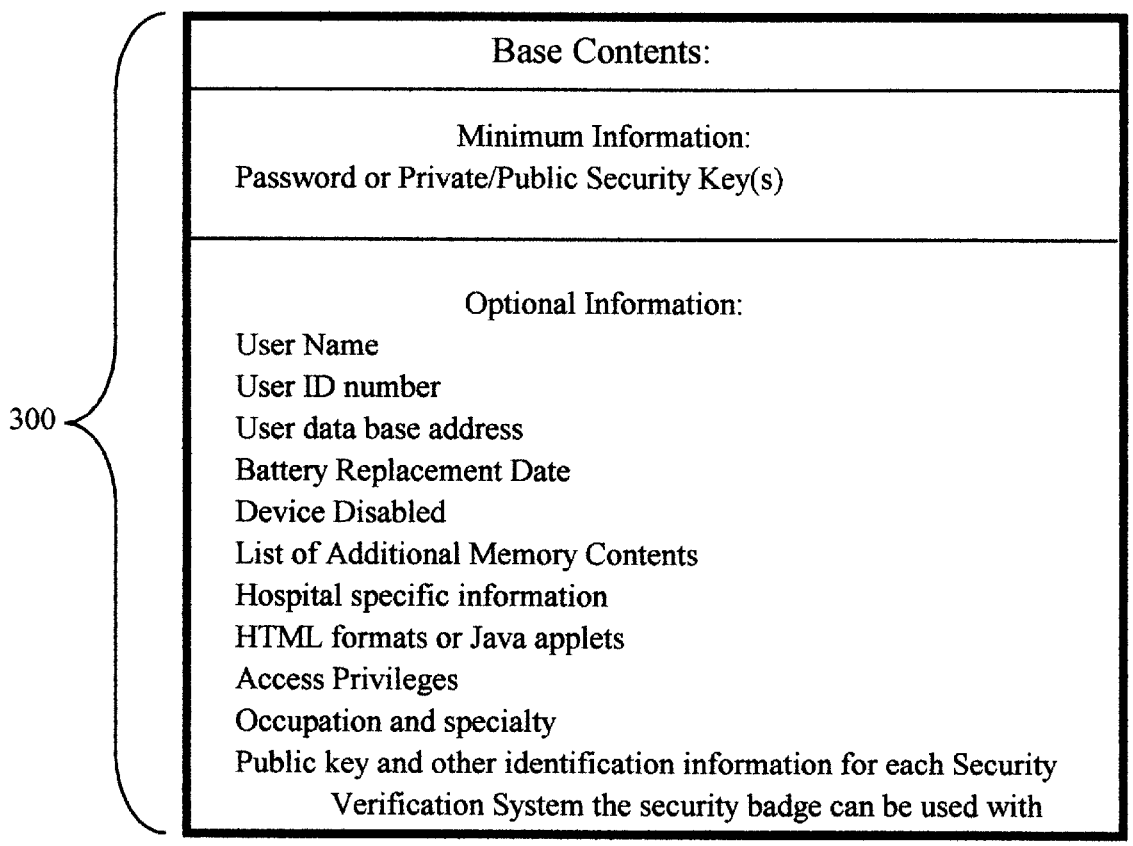
FIG. 8 presents the base memory contents of a security badge.

FIG. 6 sets forth a diagram of the processor circuitry 260 of the security badge 10, which includes a processor 250 which may be linked to several of the following: a battery 252, a real-time clock 254 to provide the current time and date, a memory element 262, an audible alerting device 20, infrared transmitter and detector device 22, a dictation button 26, and a display 258 such as a light emitting diode array, an LCD screen, or a passive or active matrix screen. An illustration of certain "base contents" 300 that may be stored by the memory element 262 is set forth in FIG. 8.

Figure 7:
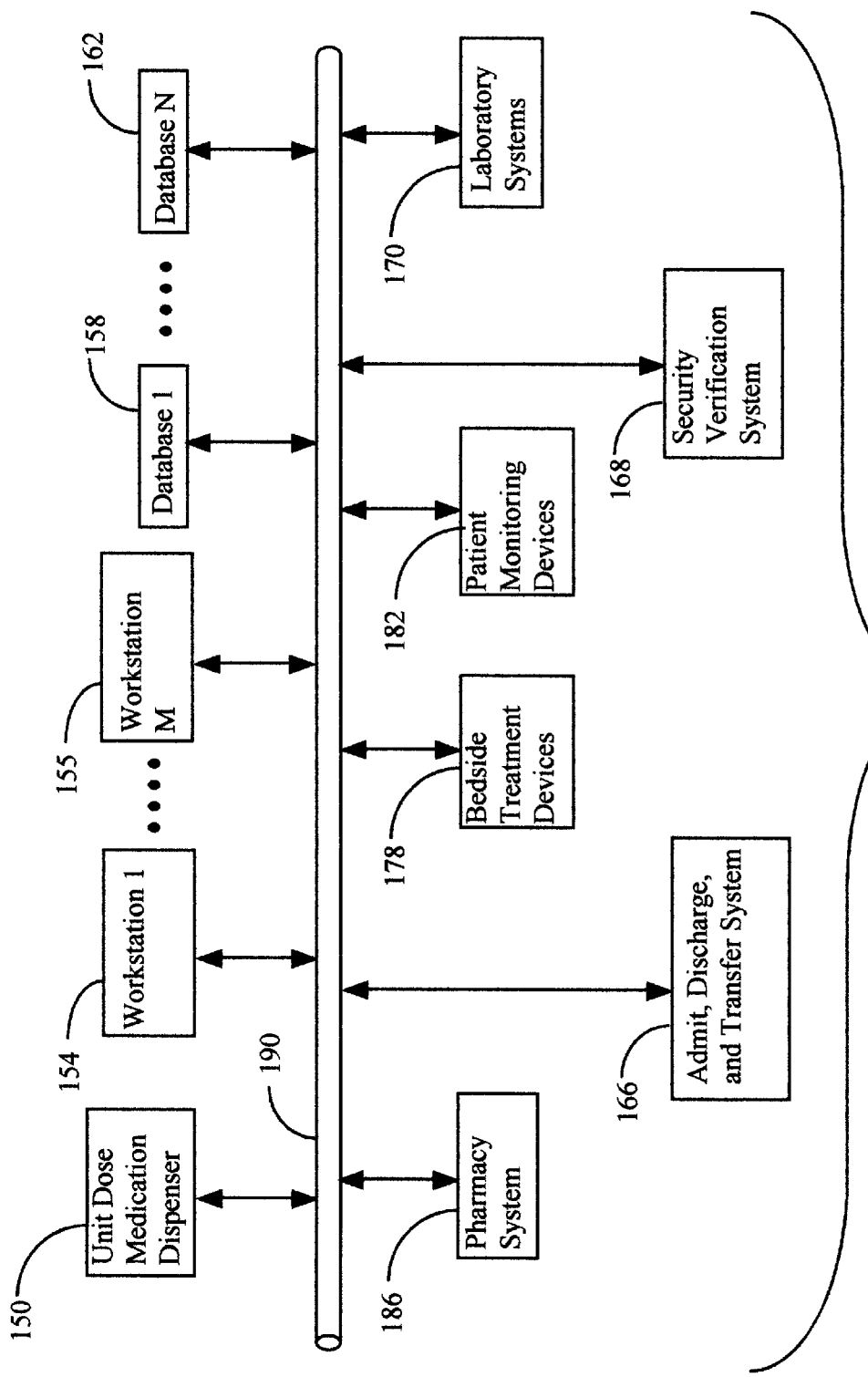
FIG. 7 is a block diagram of a computer network according to the present invention, including a plurality of workstations and databases for data record retrieval and storage and a security verification system.

Referring now to FIG. 7, the overall system of the preferred embodiment is illustrated as an electronic system referred to as computer network 194, including a plurality of personal computers or computer terminals comprising workstations 154 and 155 (designated "Workstation 1" and "Workstation N"), which may be located in patient rooms, nurse stations, doctor offices, and administrative offices; a plurality of databases comprising databases 158 and 162 (designated "Database 1" and "Database N"); an Admit, Discharge, and Transfer (ADT) system 166; at least one laboratory system 170; various bedside treatment devices 178 such as ventilators and IV infusion pumps; patient monitoring devices 182; a pharmacy system 186; a security verification system 168; and a unit dose medication dispenser 150. The individual components of the computer network 194 may communicate with each other via a communication network 190, which may comprise a combination of local and wide area networks, using ethernet, serial line, token ring, wireless, or other communication standards. Communication network 190 may also be arranged in such a manner to be part of the Internet or as an individual Intranet. The functions performed by the various components of the preferred embodiment of the computer network 194 may be divided among multiple computer systems or consolidated into fewer components.

A. Operation of a Computer Terminal in Access Control

In the preferred embodiment, authentication and data security will be illustrated through the use of conventional "public key" cryptography, such as that implemented in RSA, though other well-known techniques for authenticating a user and securing transmitted data may be employed. In implementing public key cryptography, the security badges and computer terminals are equipped with "private key rings" of one or more private keys and a "public key ring" of one or more public keys. Depending upon their sophistication and the sensitivity of the information they contain, other smart devices in the hospital, such as monitoring devices or medical instruments, may also be equipped with cryptographic means. The private keys of each security badge 10 are never transmitted or otherwise made accessible outside the security badge 10. For strong compression, each public and private key would typically be at least 128 bytes long. Today, the preferred implementation for smart card encryption capabilities utilizes the Advanced RISC Microprocessor (ARM), such as the ARM 6, the ARM 710, or a variety of customized chips integrating the ARM technology, such as the Mykronics Capstone or VLSI's VMS 210. A variety of other processors, including the Intel x86 processor, would also be suitable.

FIGS. 15A–15F describe the operation of a computer terminal 60 (FIG. 3) in establishing and monitoring access by a system user 68 wearing a security badge 10 (FIG. 1). Access is established by providing a substantially unobstructed signal path between the physical wireless communication means 14 (FIG. 1) (preferably comprising infrared transmitter and receiver components (see FIG. 1)) of the security badge 10 and the wireless transceiver device 64 of the computer terminal 60. The establishment of an unobstructed signal path is facilitated by having the security badge 10 worn on or attached to the front of the system user 68 attempting to logon the computer terminal 60. While it is not necessary that the security badge 10 be worn by or attached to the clothing of the system user 68, securing the security badge 10 to the system user 68 minimizes the probability that it will be lost by the system user 68.

Figure 15A:
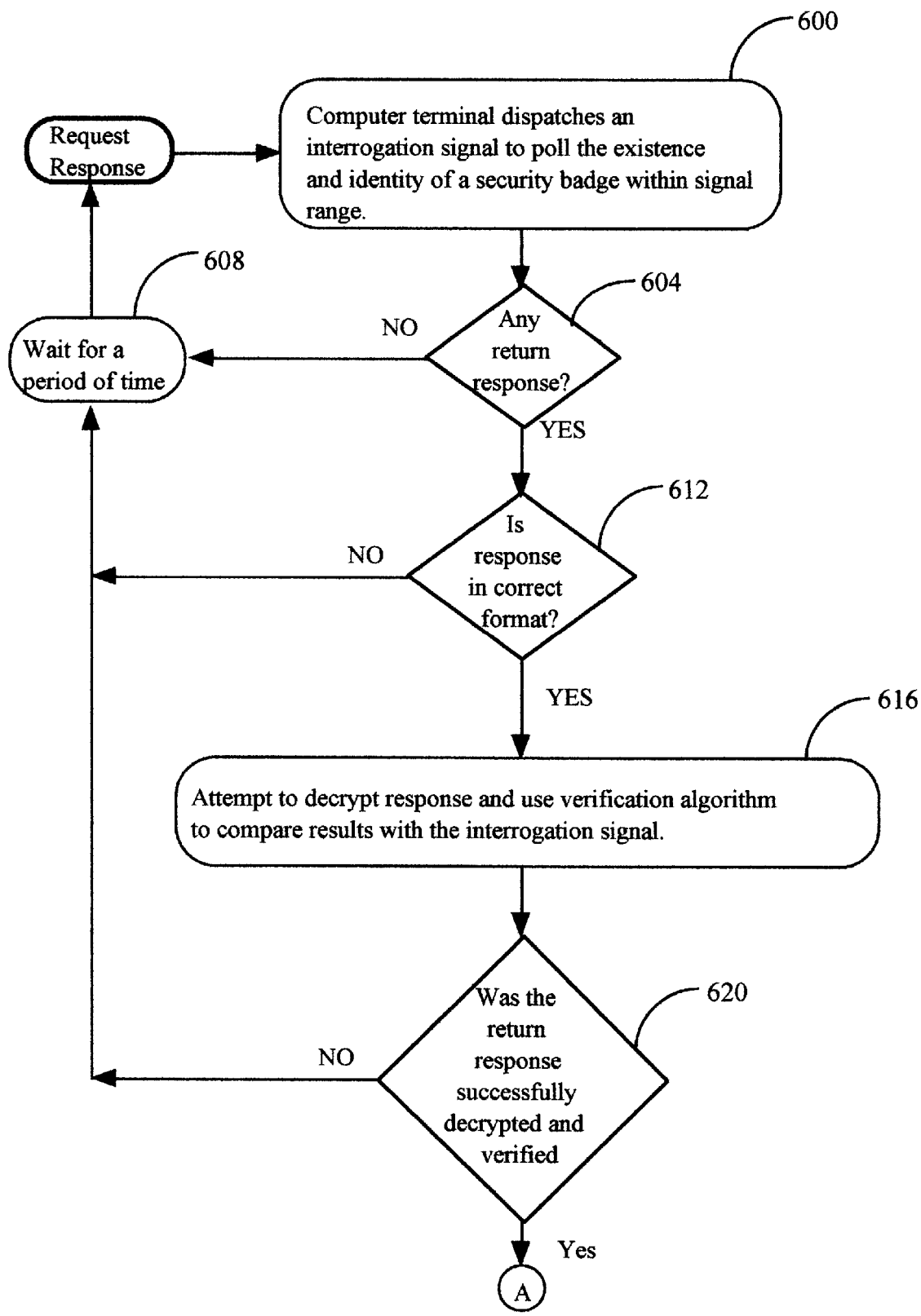
FIGS. 15A–15F are a functional flow chart showing the steps a computer terminal executes in logging on a system user using a security badge for identification.
Figure 15B:
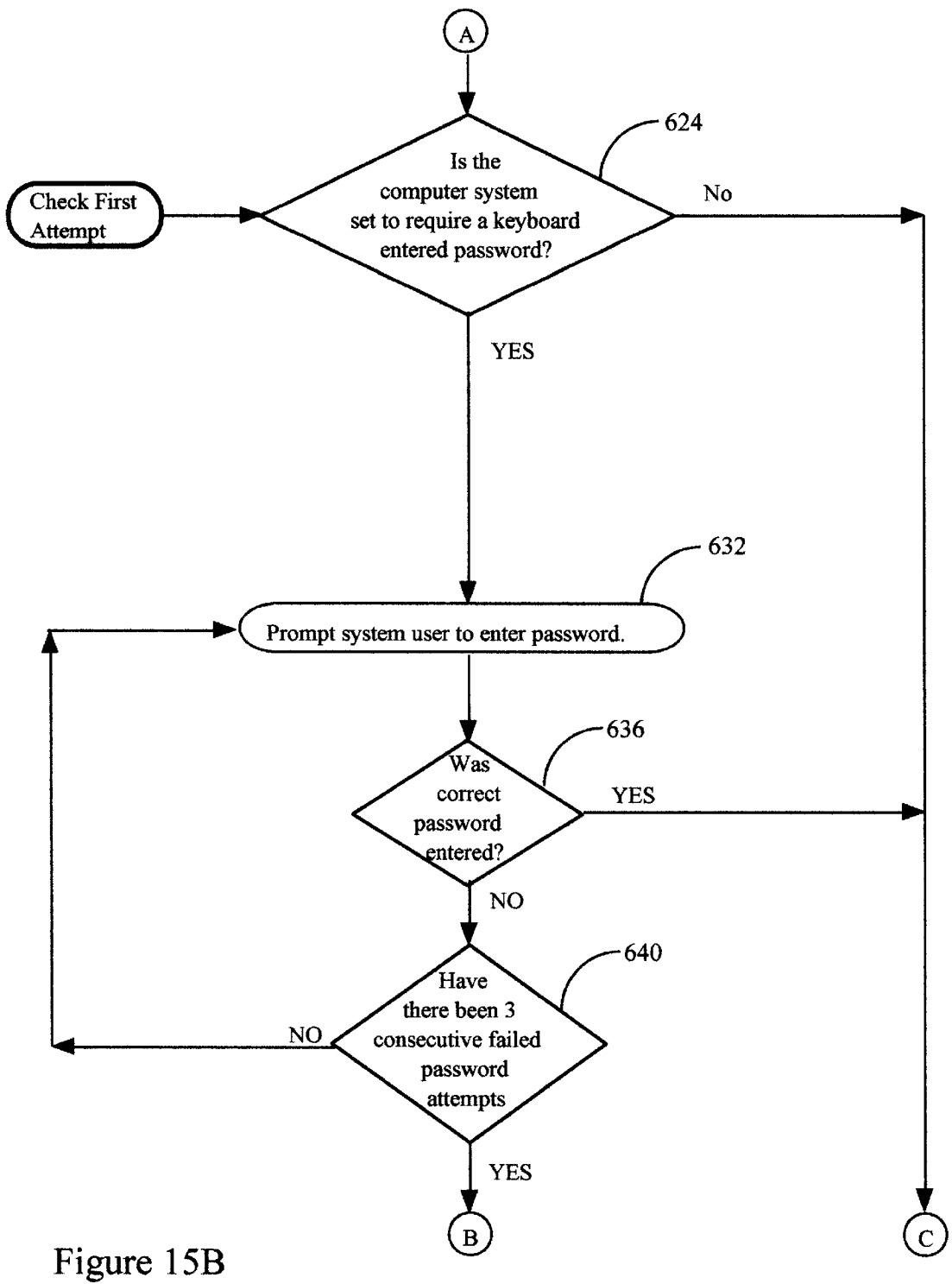

Commencing with FIG. 15A, in step 600 the computer terminal 60 transmits an interrogation signal, which is fashioned from a private key of the security verification system 168 (FIG. 7) of the computer network 194, a large random number, and other identification information unique to the security verification system 168. Provided a substantially unobstructed signal path exists between the wireless transceiver device 64 (FIG. 3) of the computer terminal 60 and the wireless communication means 14 (FIG. 1) of a security badge 10, the security badge 10 will intercept, process, and be operable to return a part of the interrogation signal in a re-encrypted form (according to the operation of the security badge 10 set forth in FIGS. 16A–16F, infra).

In step 604, the computer terminal 60 waits for a period sufficient to allow a security badge 10 to receive, process, re-encrypt, and re-transmit the interrogation signal. If no return response is received, in step 608 the computer terminal 60 waits for a predetermined period of time and, returning to step 600, transmits another interrogation signal. If a return response is received, in step 612 the format of the return response is evaluated. If the format is unrecognized, in step 608 the computer terminal 60 waits for a predetermined period of time and, returning to step 600, transmits another interrogation signal.

If a return response of a recognized format is received by the computer terminal 60, in step 616 it is decrypted or authenticated using the public key of the security badge 10 which returned the response. In a public key cryptographic system, encryption with a private key uniquely identifies the system user 68 possessing that key (assuming the private key has not been stolen) because an encrypted message can only be decoded using the public key matching the system user 68's private key. Accordingly, the security verification system 168, which stores the public keys of each security badge 10 given access privileges to the computer network, attempts to decrypt the re-encrypted interrogation signal using the public keys it retains.

There are at least two ways in which the decryption procedure may be carried out. In one procedure, the security verification system 168 attempts to decrypt the response signal, one public key at a time, until either a successful decryption is achieved or all the public keys stored by the security verification system 168 fail. Preferably, however, the identification information will have been appended to the encrypted portion of the return response purporting to identify the security badge 10. The security verification system 168 then attempts to decrypt the return response using the public key corresponding to the appended identification information. A successful decryption identifies the security badge 10 that originated the return response. If the decryption is successful, a verification algorithm is used to compare the decrypted return response to the original, pre-encrypted interrogation signal.

It would, of course, be possible to program the computer terminal 60 itself to perform some or all the functions of the security verification system 168. A physically separate security verification system 168, however, will safeguard the computer network 194's private keys and the list of public keys of valid system users, preventing appropriation of the keys by one breaking into the computer terminal 60 itself.

As an additional precaution, the security badge 10 may be programmed to detect and reject interrogation signals that are short and probabilistically non-random. This would frustrate a cryptanalyst's attempt to derive a security badge 10's private key by interrogating the security badge 10 with short messages and intercepting the re-encrypted response. This precaution is especially justified if the security badge 10 is adapted to communicate with devices and computer terminals foreign to the computer network 194 and its security verification system 168. This precaution may also limit the damage that could be imposed were a private key of the security verification system 168 compromised.

In step 620, if the decryption and verification failed to identify a security badge 10 having access privileges to the computer terminal 60, then the operation proceeds again to step 608, where the computer terminal 60 waits for a predetermined period of time and, returning to step 600, transmits another interrogation signal.

Because a security badge 10 may be misplaced by or stolen from a system user 68, additional security measures are warranted. The security verification system 168 may be programmed to require that a system user 68 manually enter a password at the beginning of each day. Alternatively, the system could require manual password entry at random times throughout the day, even while the system user 68 is logged on, flagging possible theft and unauthorized use of the security badge 10 should the proper password not be detected. Further, a switch may be incorporated onto the security badge 10 to force it into a mode requiring password entry. More elaborate means, including voice identification or a fingerprint or retinal scan, could also be incorporated into the security badge 10 or at computer terminals 60 to reinforce such security. It is to be expected, however, that should a system user 68 be dispossessed of a security badge 10, that he or she immediately notify the system security administrator to deactivate the access privileges of the security badge 10.

Provided a security badge 10 having access privileges to the computer terminal 60 has been identified, in step 624 the security verification system 168 determines whether or not to require the entry of a password to enable logon by the system user 68. This procedure provides a safeguard should the security badge 10 be stolen, deterring unauthorized logon attempts with the threat that the security verification system 168 will detect the breach and apprehend the violator.

If password entry is required, then in step 632 the computer terminal 60 prompts the system user 68 for a password. Information that is entered may not only be processed by the computer terminal 60, but also transmitted to the security badge 10 in encrypted form in order to reset a flag maintained by the security badge 10 indicating that password entry is required. In step 636, the password is analyzed. If the wrong password has been entered, in step 640 a counter is incremented. If the wrong password was entered less than three consecutive times (step 640), the security verification system 168 returns to step 632 and again prompts the system user 68 to enter the password. After three failed attempts (step 640), however, in step 644, the security verification system 168 disables recognition of the security badge 10, records the location of the failed attempt, and notifies the system administration to alert it to a possible attempted breach of the system.

If within the first three attempts, the correct password is entered, the operation advances to step 648, logging the system user 68 onto the computer terminal 60 and providing access to program features and databases in accordance with the access privileges of system user 68. In step 652, the computer terminal queries the security badge 10 for the existence of data records to transfer to the computer network 194 and causes the security badge 10 to transmit them, if any, to the computer terminal 60 for database storage, in accordance with the operation detailed in FIGS. 16A–16F.

After the completion of the data transfer, if warranted, by the security badge 10 to the computer terminal 60, the computer terminal 60 will continue to periodically poll the security badge 10 with recommitment signals. These recommitment signals may be specifically addressed to the system user 68's security badge 10 and may incorporate a different random number with each polling. Further, these recommitment signals may be encrypted with the security badge 10's public key stored by the security verification system 168, instead of or in addition to encryption by the security verification system's private key, so that they may only be intelligibly decrypted by the security badge 10 itself, using its own exclusively-guarded private key. By periodically polling the security badge 10, the user input and output devices of the computer terminal 60, including the monitor, keyboard, and mouse, can be disabled if the computer terminal ceases receiving response signals from the security badge 10. A system user 68 may also be automatically logged out by means of periodic polling.

Figure 15C:
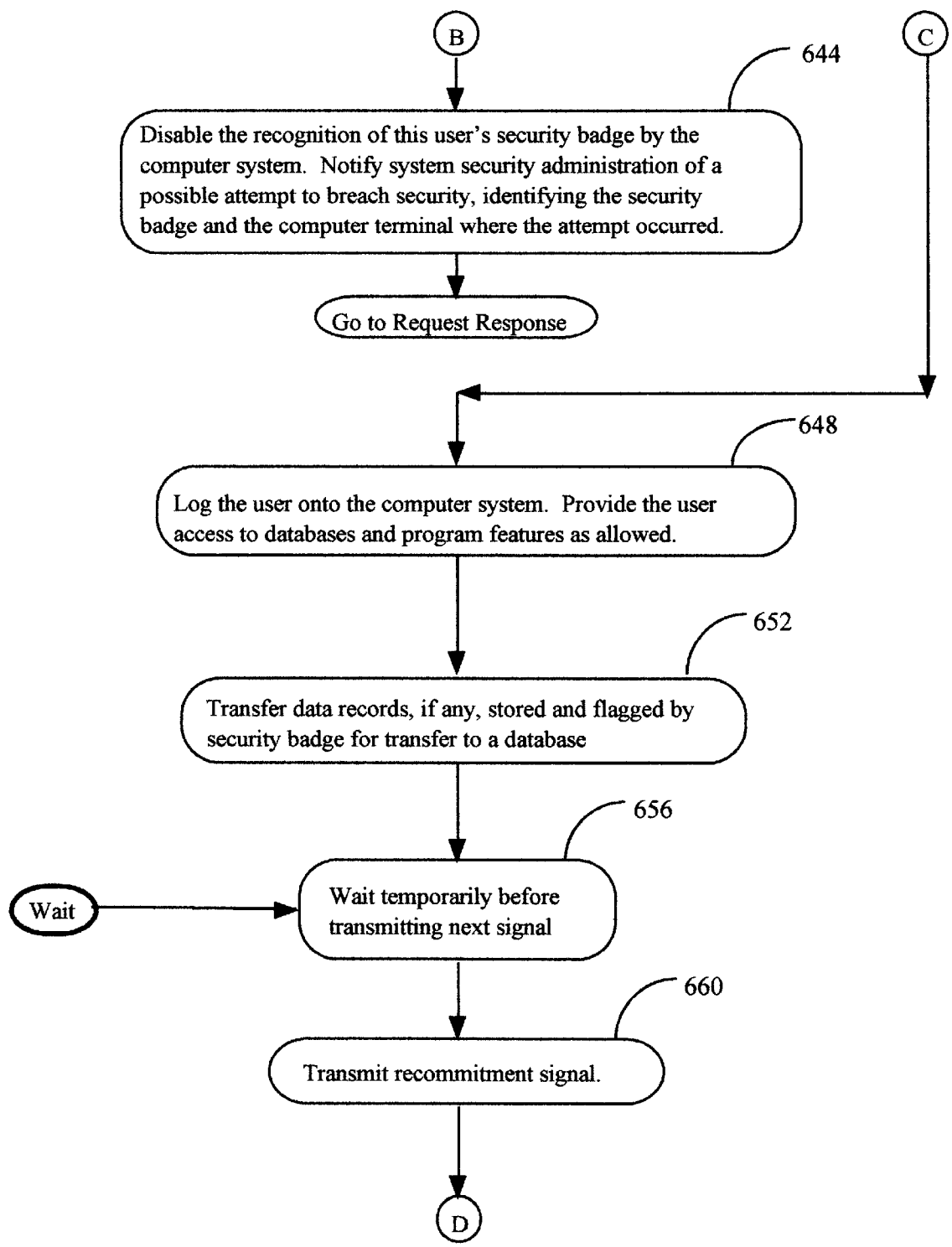
Figure 15D:
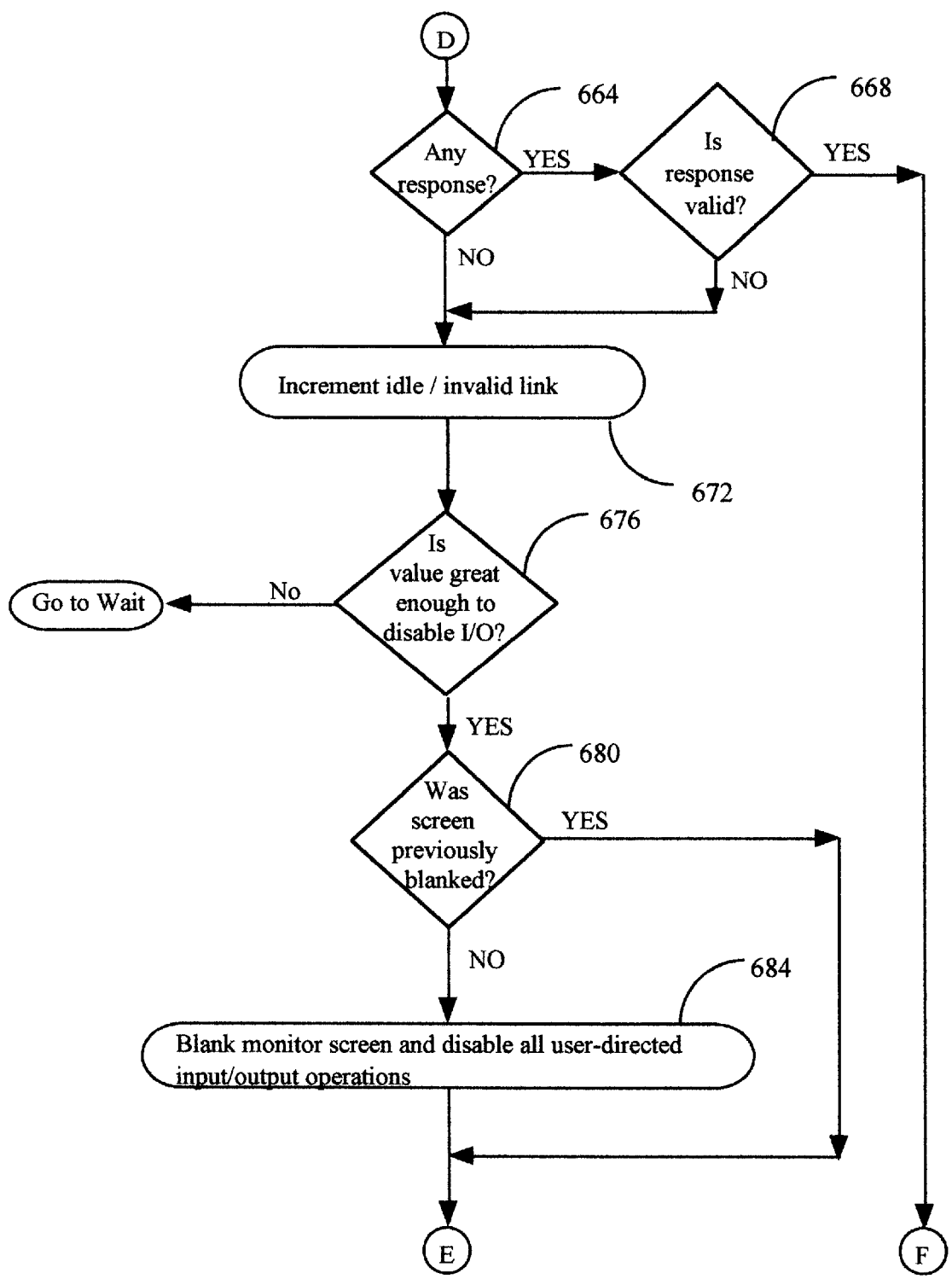
Figure 15E:
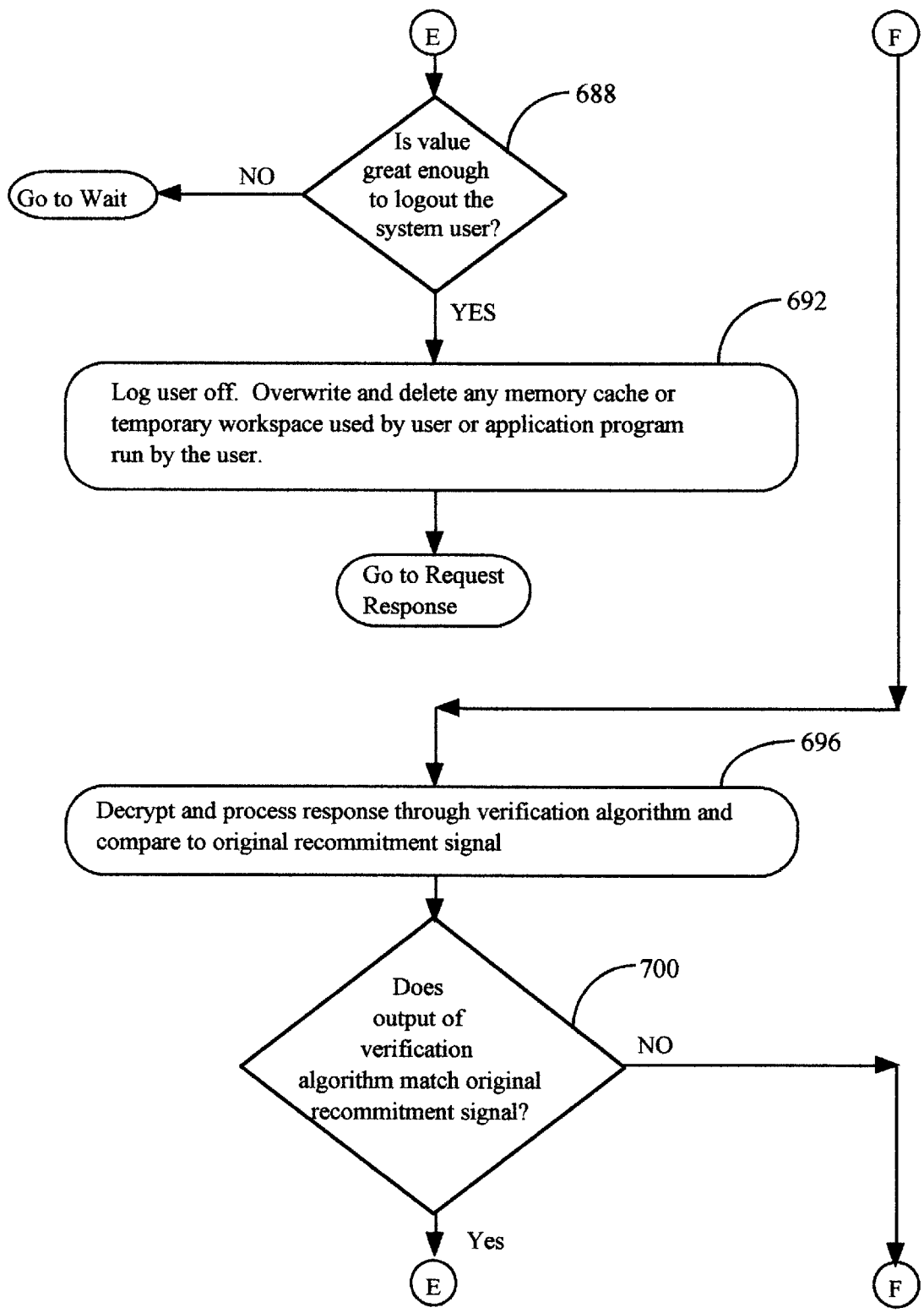
Figure 15F:
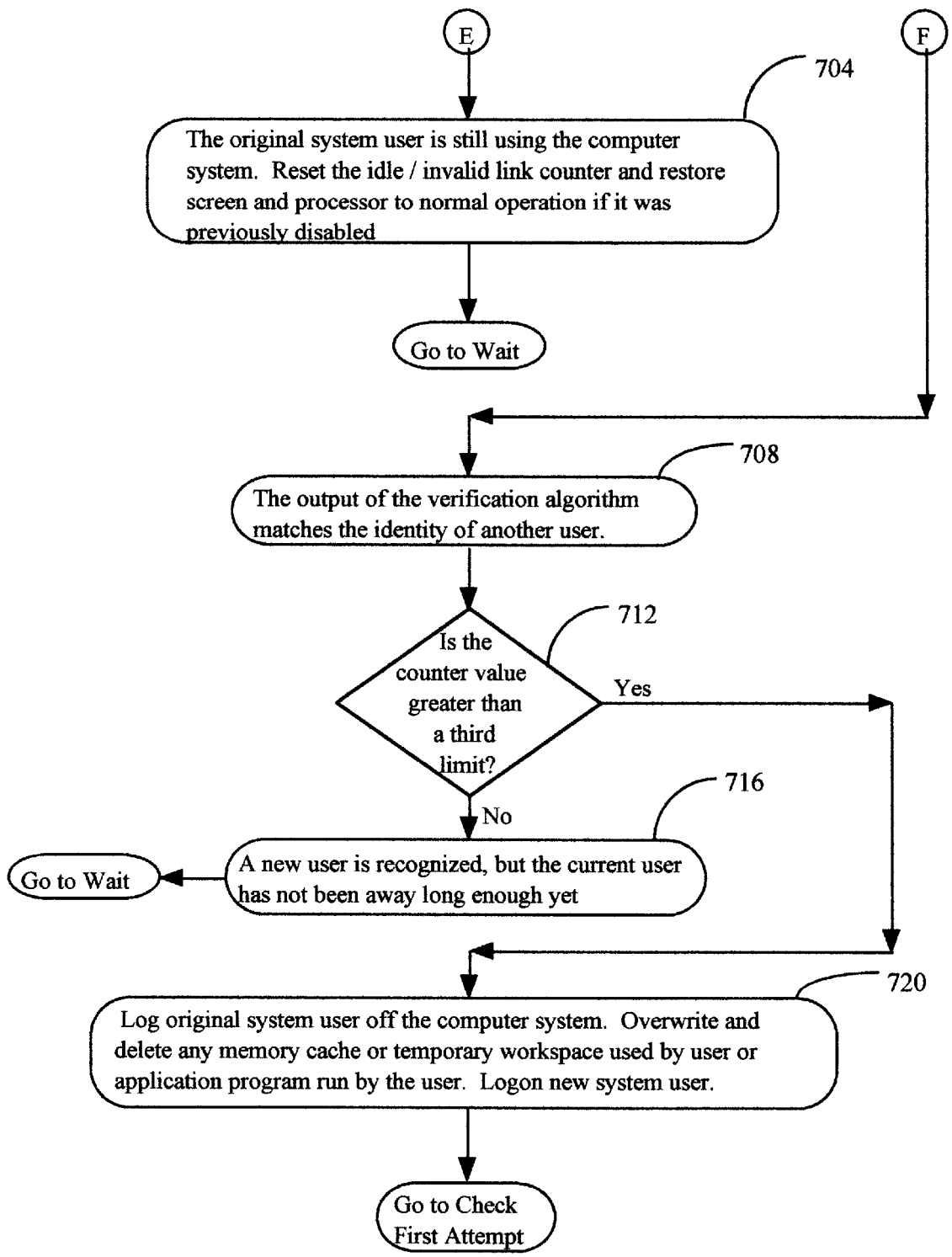
Figure 16A:
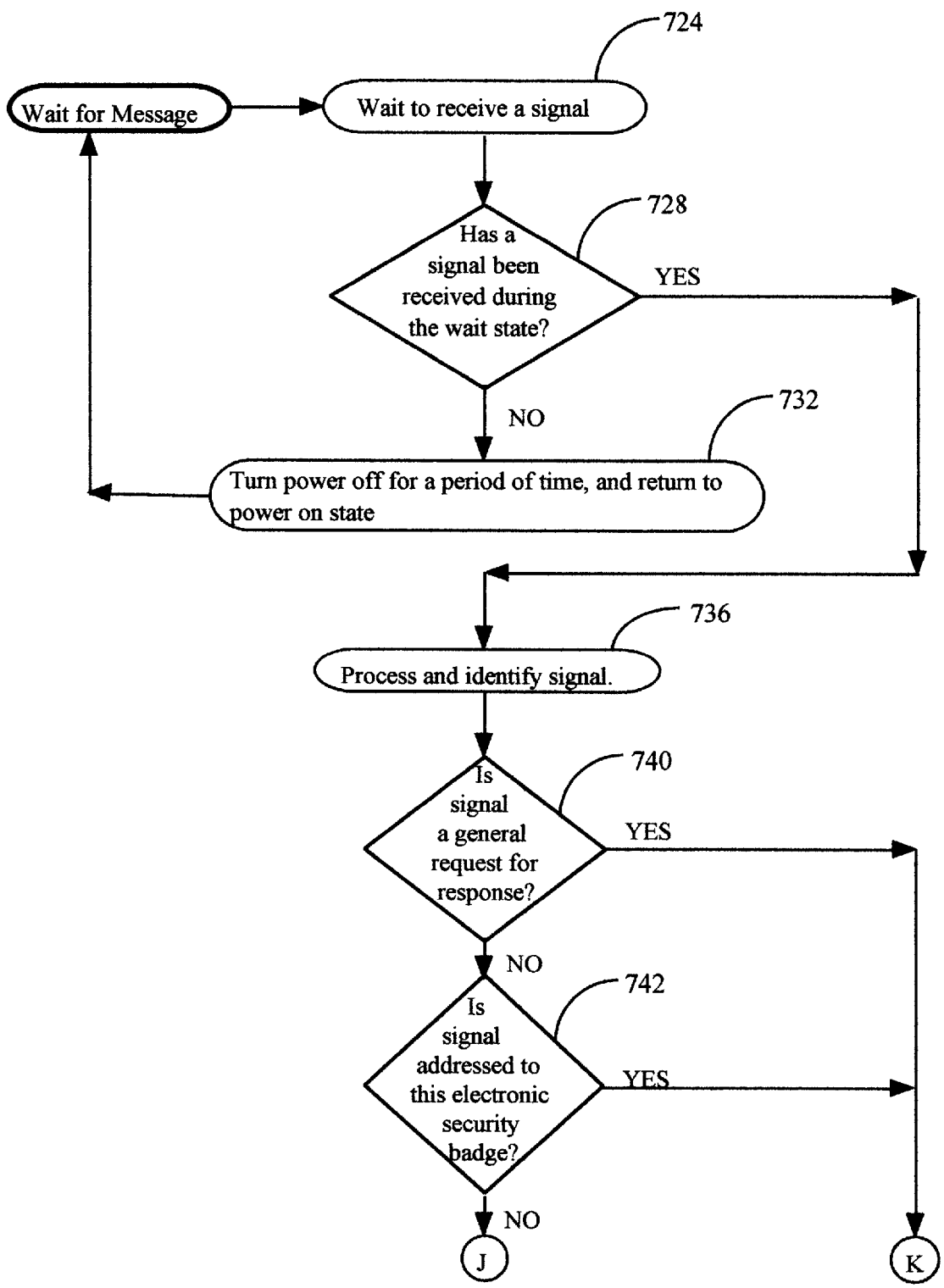
FIGS. 16A–16F are a functional flow chart showing the steps a security badge executes in logging on to a computer system, sending data, or signing a document.
Figure 16B:
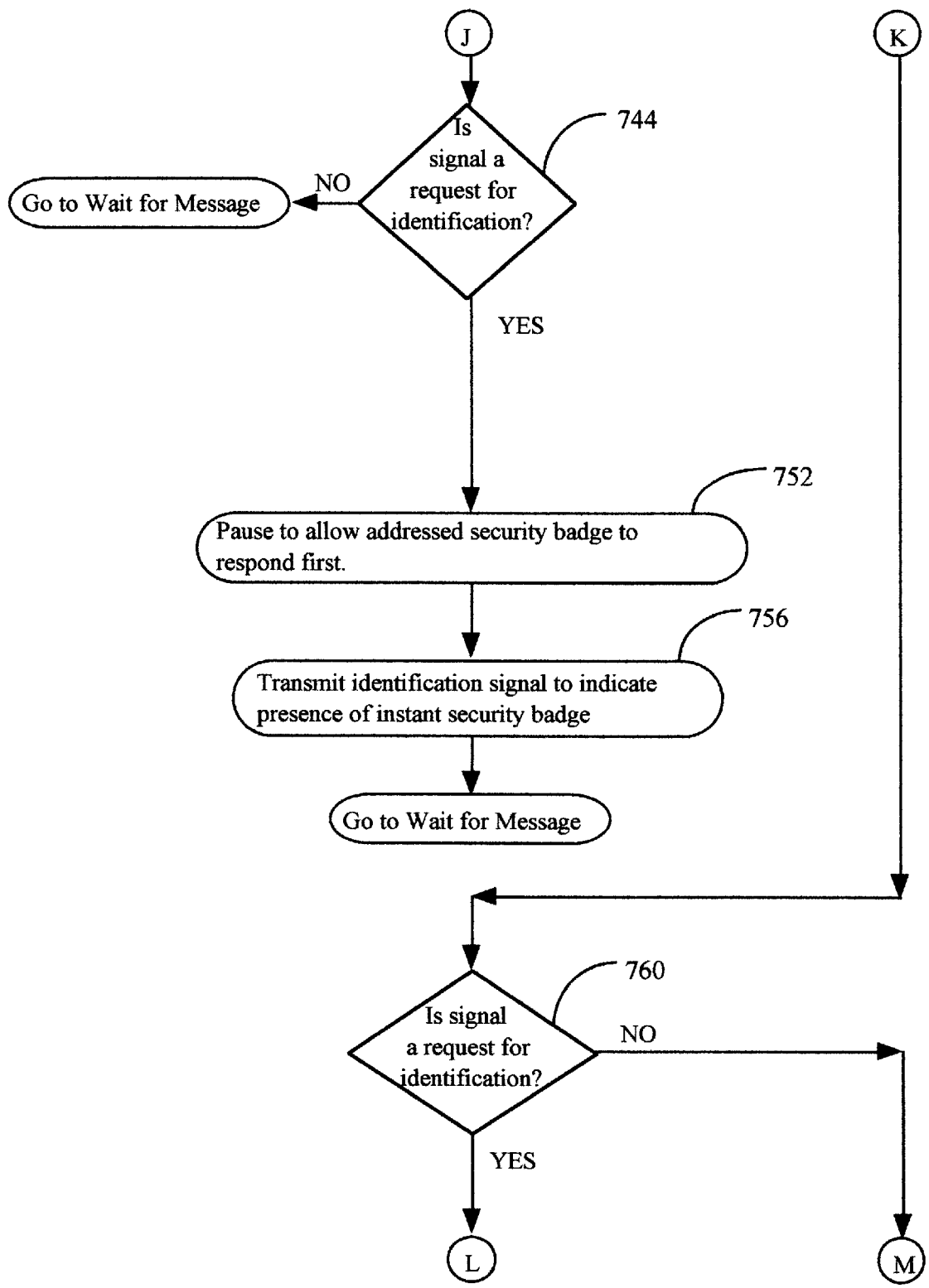
Figure 16C:
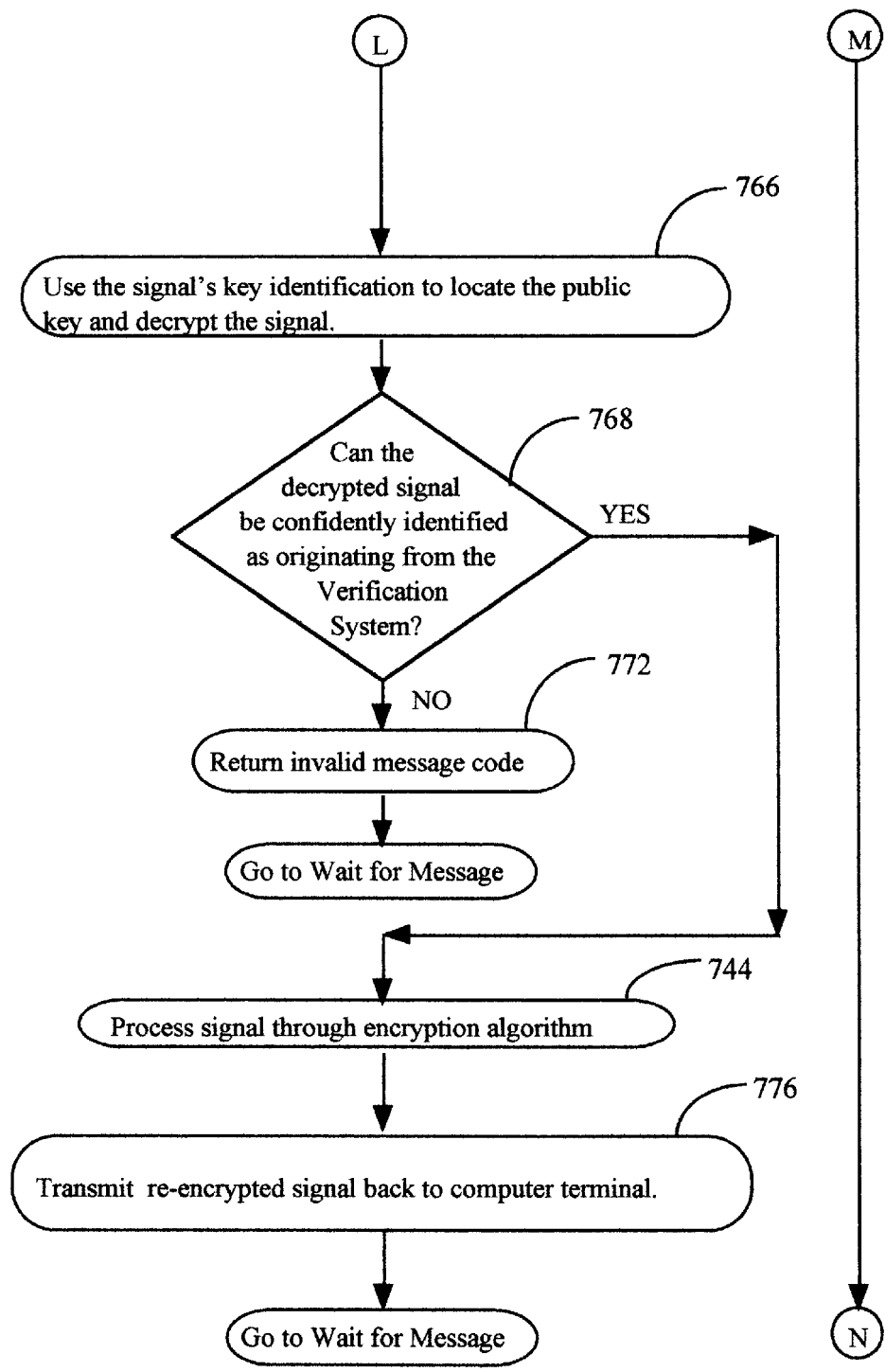
Figure 16D:
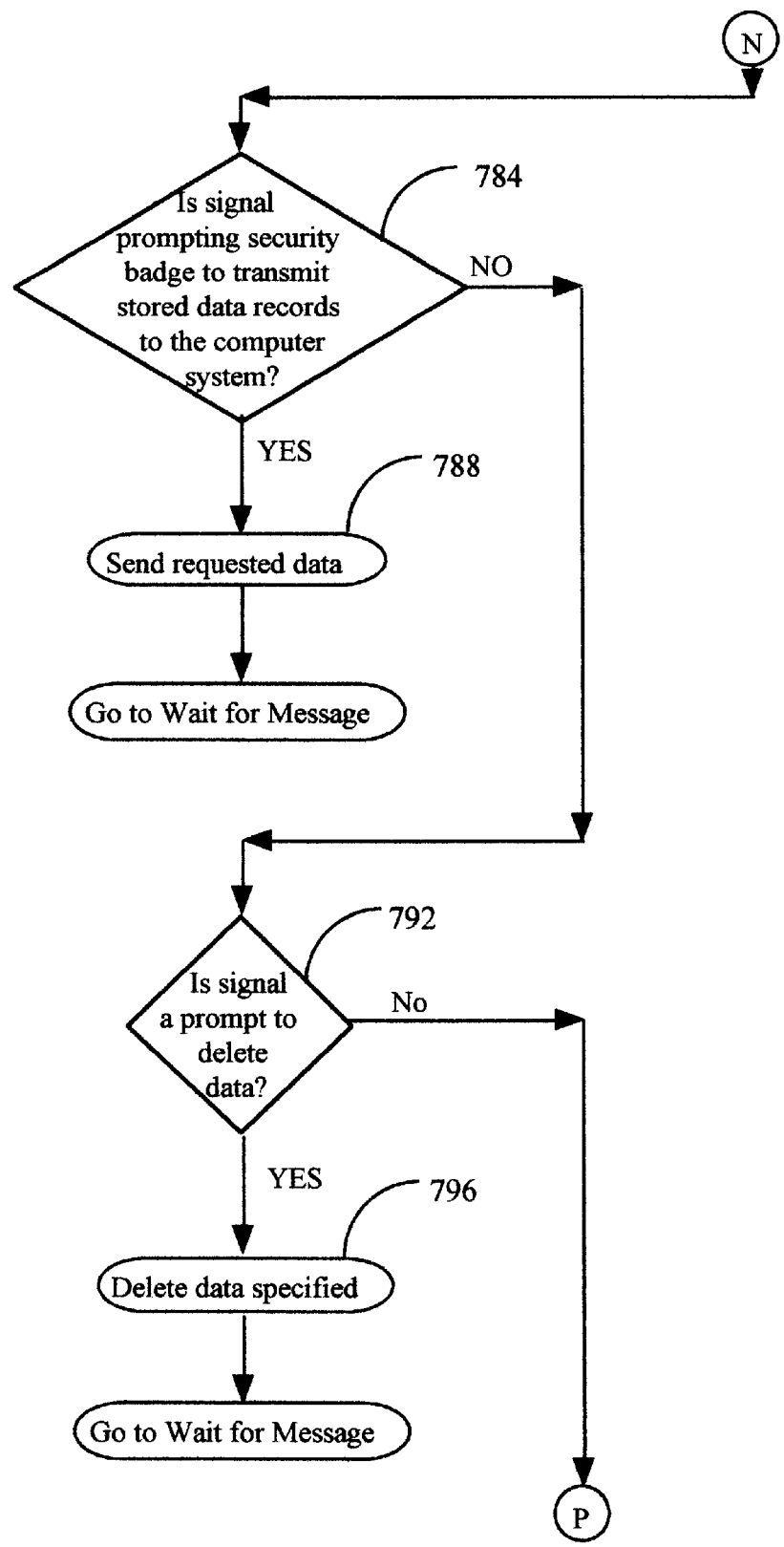
Figure 16E:
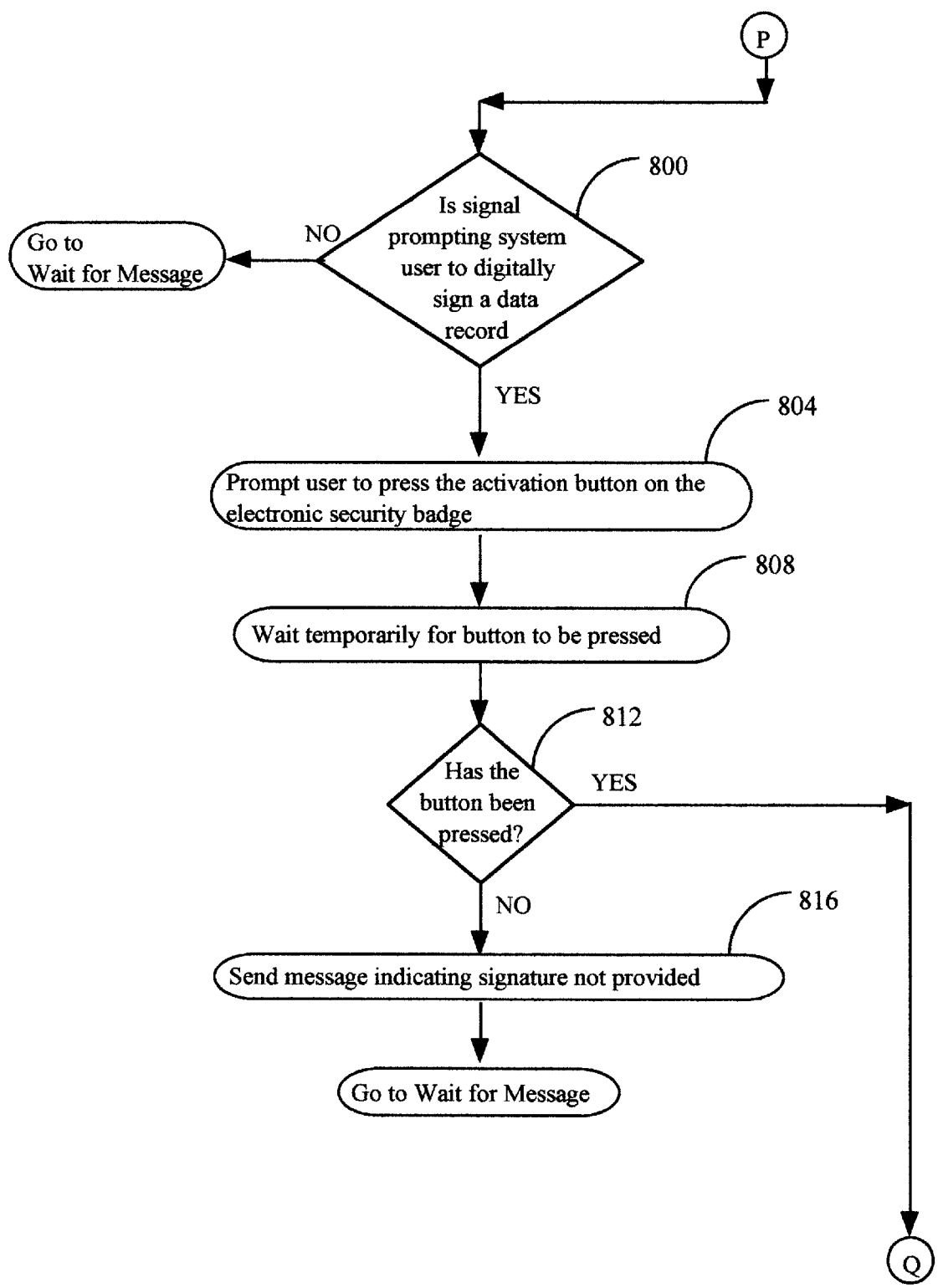
Figure 16F:
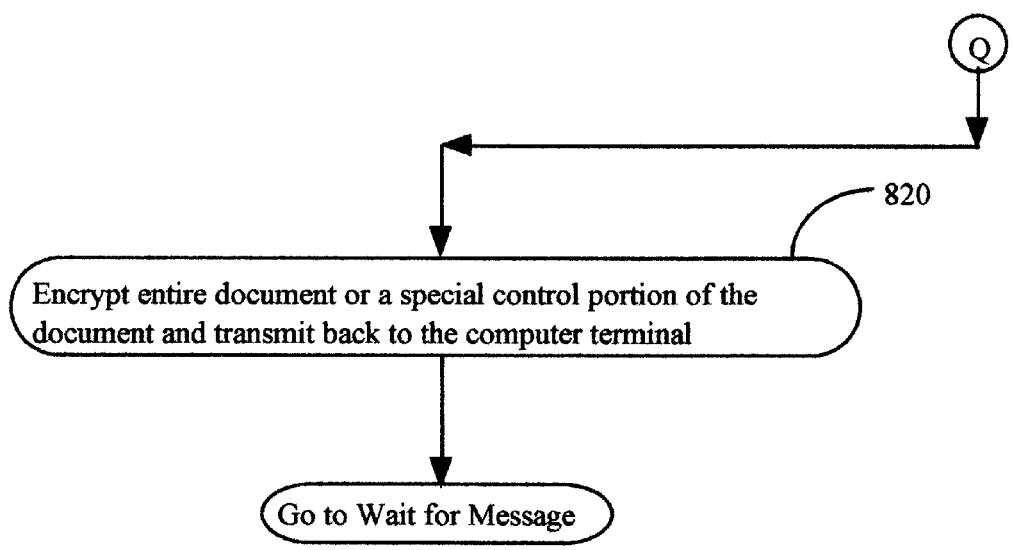

This process of periodic polling is illustrated in steps 656 through 692 of FIGS. 15C–15E. The computer terminal waits for a predetermined interval in step 656, transmits a recommitment signal in step 660, and probes for a response signal in step 664. If there is a recommitment response signal, in step 668 its content is evaluated. If the content of the recommitment response signal is accepted, the operation proceeds to step 696, discussed infra. If either there is no recommitment response signal in step 664, or if the content of the recommitment response signal is rejected in step 668, an idle/invalid link counter (not illustrated) maintained by the security verification system 168 and whose initial value relative to the logon event was zero, is incremented in step 672.

The idle/invalid link counter permits the system user 68 to temporarily turn away from the transceiver device 64 of the computer terminal 60 or to otherwise interfere with the signal path. However, if the computer terminal 60 does not receive a recommitment response signal after several requests, the display of the computer terminal 60 is blanked, input from any keyboard or pointing device may be ignored, and other processing activities may be suspended. The computer terminal 60, however, continues to transmit recommitment signals. Should the system user 68's security badge 10 respond within a second period of time, the display will be restored to its previous condition and the keyboard, pointing device, and processor will resume normal operation. If the security badge 10, however, does not transmit a correct recommitment response signal during the second period of time, the system user 68 is automatically logged off the computer network 194. When the user is logged off the computer system, a software program may also be used to remove any temporary files that have been stored on disk or in RAM memory, e.g. the cache file used by the network browser program. Furthermore, access by the computer terminal 60 to the computer network 194 may be terminated with the exception of the link between the computer terminal 60 and the security verification system 168, which may be preserved to determine if a new user is attempting to use the computer terminal 60 to log onto the computer network 194. In this manner a system user 68's access to the computer network 194 is restricted while logged off and enlarged while logged on.

This computer terminal access security operation is described more particularly in steps 676 through 692 of FIGS. 15D–15E The value of the idle/invalid link counter is compared in step 676 to a predetermined disable I/O limit. If that value does not exceed the disable I/O limit, the periodic polling continues with step 656. If and when the value of the idle/invalid link counter does exceed the disable I/O limit, in step 684, the input and output devices of the computer terminal 60 are disabled, if they have not been previously disabled (step 680). In step 688, the value of the idle/invalid link counter is compared to a predetermined logout limit. Periodic polling is continued in step 656 if the value of the idle/invalid link counter does not exceed the logout limit. If and when this value is exceeded, in step 692 the system user 68 is logged off the computer terminal 60 and information stored in memory or cache on the computer terminal by the user is overwritten.

If the content of the recommitment response signal is valid (step 668), in step 696 the security verification system 168 processes the signal through a verification algorithm, attempting to decrypt the signal with public keys and comparing the decrypted output with the original recommitment signal. If the decrypted output matches the original recommitment signal (step 700), then in step 704 the computer network 194 recognizes that the system user 68 is still using the computer system. The idle/invalid link counter is reset and the display and other input and output functions of the computer terminal 60, if disabled, are restored. If the decrypted output does not match the original recommitment signal (step 700), then in step 708 the computer network 194 recognizes that another system user 68 is nearby. If the value of the idle/invalid link counter exceeds a third limit (step 712), then the original system user 68 is logged off, memory cache and temporary workspace utilized by the original system user 68 or applications executed by or through the original system user 68 is deleted and/or overwritten, and the new system user 68 is logged on to the computer terminal. If the value of the idle/invalid link counter has not yet exceeded a third limit (step 712), then the new system user 68 is recognized but not logged onto the terminal, for the original system user has not been logged off for a sufficient period of time.

B. Operation of a Security Badge in Access Control

FIGS. 16A–16F describe the operation of a security badge 10 (FIG. 1) in responding to interrogation and recommitment signals transmitted by a proximately located computer terminal 60 (FIG. 3). In order to conserve power, the security badge 10 is preferably capable of alternating between sleep and wake states. During a sleep state, the security badge 10 is not responsive to signals transmitted by computer terminals 60 and other proximate smart devices, and may be essentially "invisible" to such devices. This alternating sleep/wake cycle is described in steps 724 through 732. In step 724, the security badge 10 maintains a wake state in which it is capable of receiving and transmitting signals through its wireless communication means 14. If in step 728, the time allotted for the wake state has expired and no signal has been received via the wireless communication means 14 of the security badge 10, then in step 732 the security badge 10 is powered down for the allotted duration of its sleep state, before cycling back to the wake state of step 724.

If a signal is received during its wake state, however, the alternating sleep and wake cycle is suspended in order to process and respond to the signal. In step 736, the security badge 10 processes and identifies the signal. If the signal is identified as a nonspecifically addressed signal (step 740) or as being addressed to the instant security badge 10 processing the signal (step 742), then further evaluation of the signal is performed, beginning with step 760, discussed infra.

A signal that is neither nonspecifically addressed (step 740) nor specifically addressed (step 742) to the instant security badge 10 is regarded as being extrinsically addressed to a second security badge 10. This situation may arise when two system users 68 with two security badges 10 are in the vicinity of the same computer terminal 60, one of them being logged onto the computer terminal 60. In step 744, the extrinsically addressed signal is evaluated to determine whether or not it is of a nature seeking an identification signal from the second security badge 10. If not, the instant security badge 10 ignores the extrinsically addressed signal and retires to wake state 724. If, however, the extrinsically addressed signal is of a nature requesting an identification signal, in step 752 the instant security badge 10 pauses to permit the second security badge 10 to transmit its identification signal. In step 756, the security badge 10 then transmits its own identification signal to the computer terminal 60 to indicate its presence, retiring afterward to wake state 724. This may allow the security verification system 168 to temporarily blank the screen to prevent unauthorized access to data by one system user 68 through the access privileges of another system user 68. Alternatively, after repeated failures by the computer terminal 60 to receive a response signal from the second security badge 10, the second system user 68 may be logged out and the instant system user 68 logged in.

In the event that the signal was either nonspecifically addressed (step 740) or specifically addressed to the instant security badge 10 (step 742), the operation advances to step 760, where the signal is further evaluated to determine whether it is an interrogation or recommitment signal, in which case it would have been encrypted by a private key of the security verification system 168. If in step 760 it is identified as an interrogation or recommitment signal, then in step 764, a key ID tag appended to the signal is used to locate the public key stored in the memory element 262 (FIG. 6) of the security badge 10, with which it decrypts the signal.

In step 768, the decrypted signal is evaluated for information positively or probabilistically identifying the security verification system 168 as the source of the signal. This step implements the precaution of programming the security badge 10 to detect and reject interrogation signals that are too short or probabalistically non-random. If the decrypted signal is not distinguishable as originating from the security verification system 168, then in step 772, the security badge 10 stores and transmits an invalid message code, retiring to wake state 724. If the decrypted signal is recognized as originating from the security verification system 168 (step 768), then in step 774, the signal or a portion thereof is reencrypted using the private key of the security badge 10 and transmitted, in step 776, to the computer terminal 60. Following this transmission, the security badge 10 retires to wake state 724.

Turning back to step 760, if the signal is not identified as an interrogation or recommitment signal, in step 784 the signal is evaluated to determine whether it is prompting the security badge 10 to transmit stored data to the computer terminal 60, in which case in step 788 the data is transmitted before the security badge 10 retires to wake state 724. If the signal was not identified as a prompt for data transfer (step 784), then in step 794 the signal is evaluated to determine whether it is prompting the security badge 10 to delete specified data, in which case in step 796 the specified data is deleted before the security badge 10 retires to wake state 724.

If the signal was not identified as a request to delete specified data (step 792), then in step 800, the signal is evaluated to determine whether it is prompting the security badge 10 to digitally sign a document or data record using its private key. If the signal is not identified as a request to digitally sign a document, the signal is treated as an unspecified command, upon which the security badge 10 takes no action, instead retiring to wake state 724. If the signal is identified as requesting a digital signature (step 800), in step 804 the computer terminal 60 or the security badge 10, by means of its audible alerting device 20, prompts the system user 68 to depress the activation button 18. In step 808 the security badge 10 waits for the system user 68 to respond for a limited time period. In step 812, if the activation button 18 has not been depressed before the expiration of this limited time period, then in step 816 the security badge 10 returns a signal indicating that the signature has not been provided, retiring then to wake state 724. In this manner a digital signature will not be provided without the affirmative agreement and action of the system user 68. If in step 812, the activation button 18 had been depressed within the limited time period, in step 820 the document or a message digest of the document is encrypted in whole or in part and transmitted to the computer terminal 60, the security badge 10 afterward retiring to wake state 724.

Though not illustrated, the activation button 18 may be pressed for several seconds in order to suspend automatic logon access to a computer terminal 60 without being prompted to enter a password. The security badge 10 may emit an audible sound to indicate that automatic logon has been suspended.

C. Operation of a Security Badge in Gathering Data

Figure 17A:
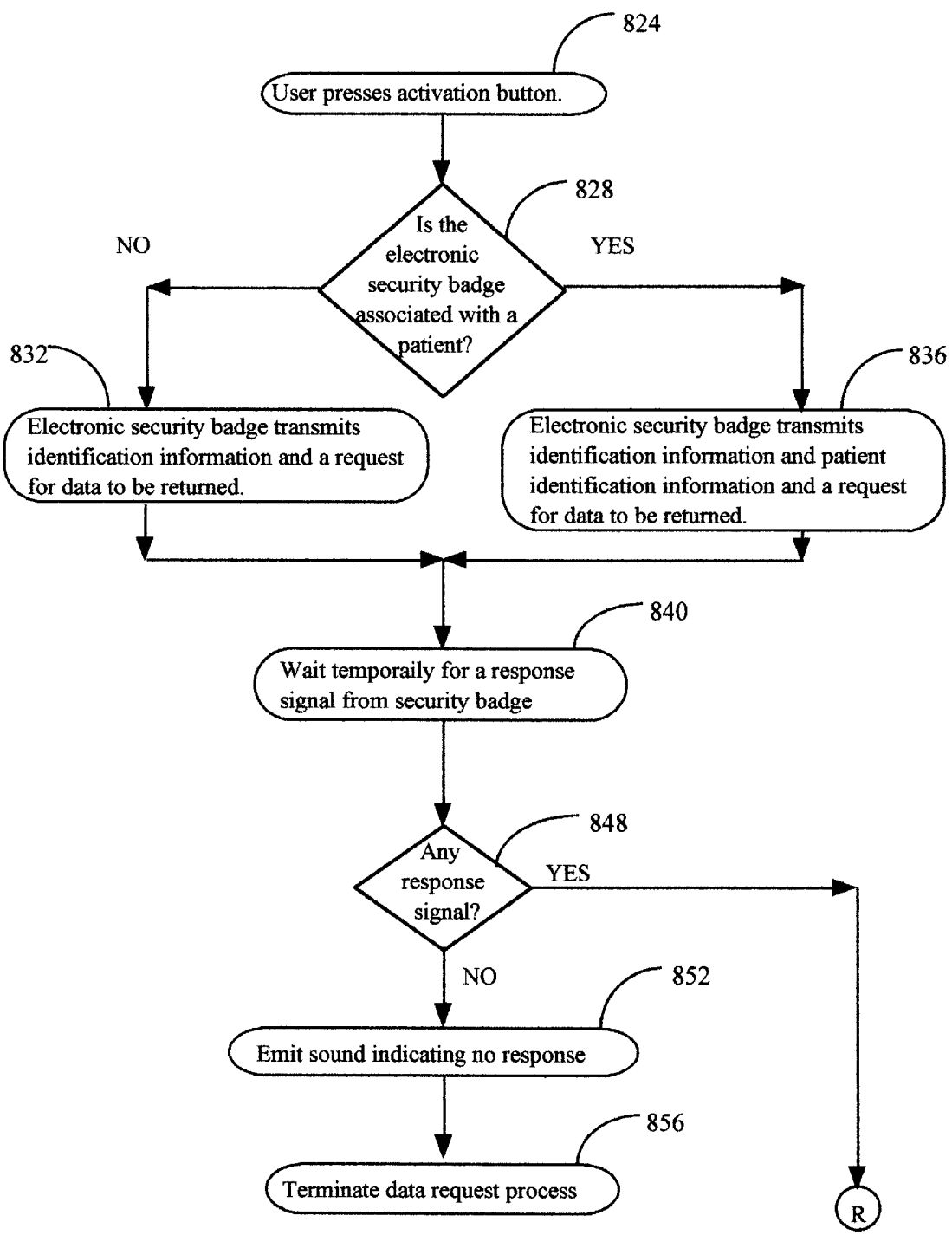
FIGS. 17A–17C are a functional flow chart of the steps a security badge executes in establishing an association with a patient and acquiring data from other computerized devices.
Figure 17B:
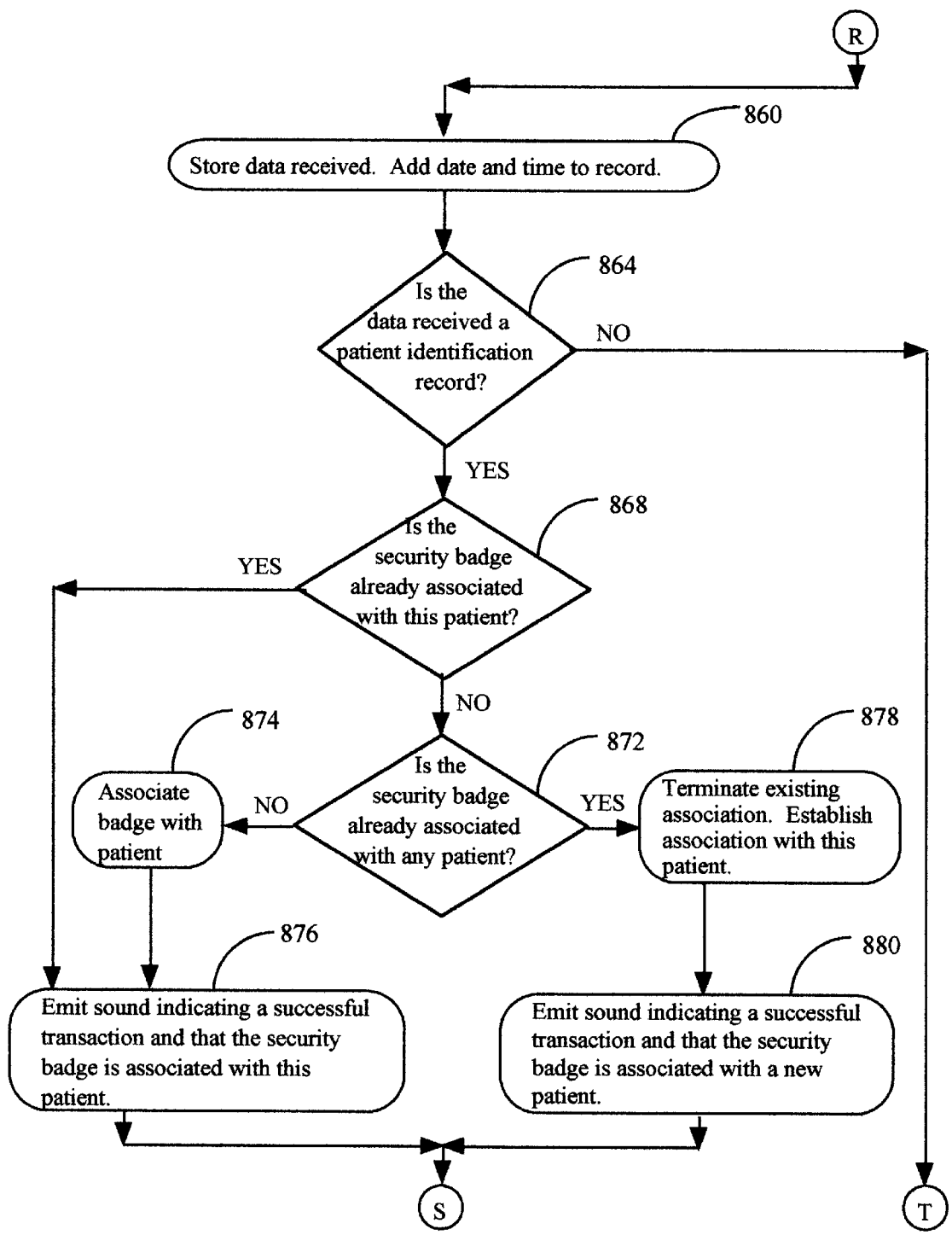
Figure 17C:
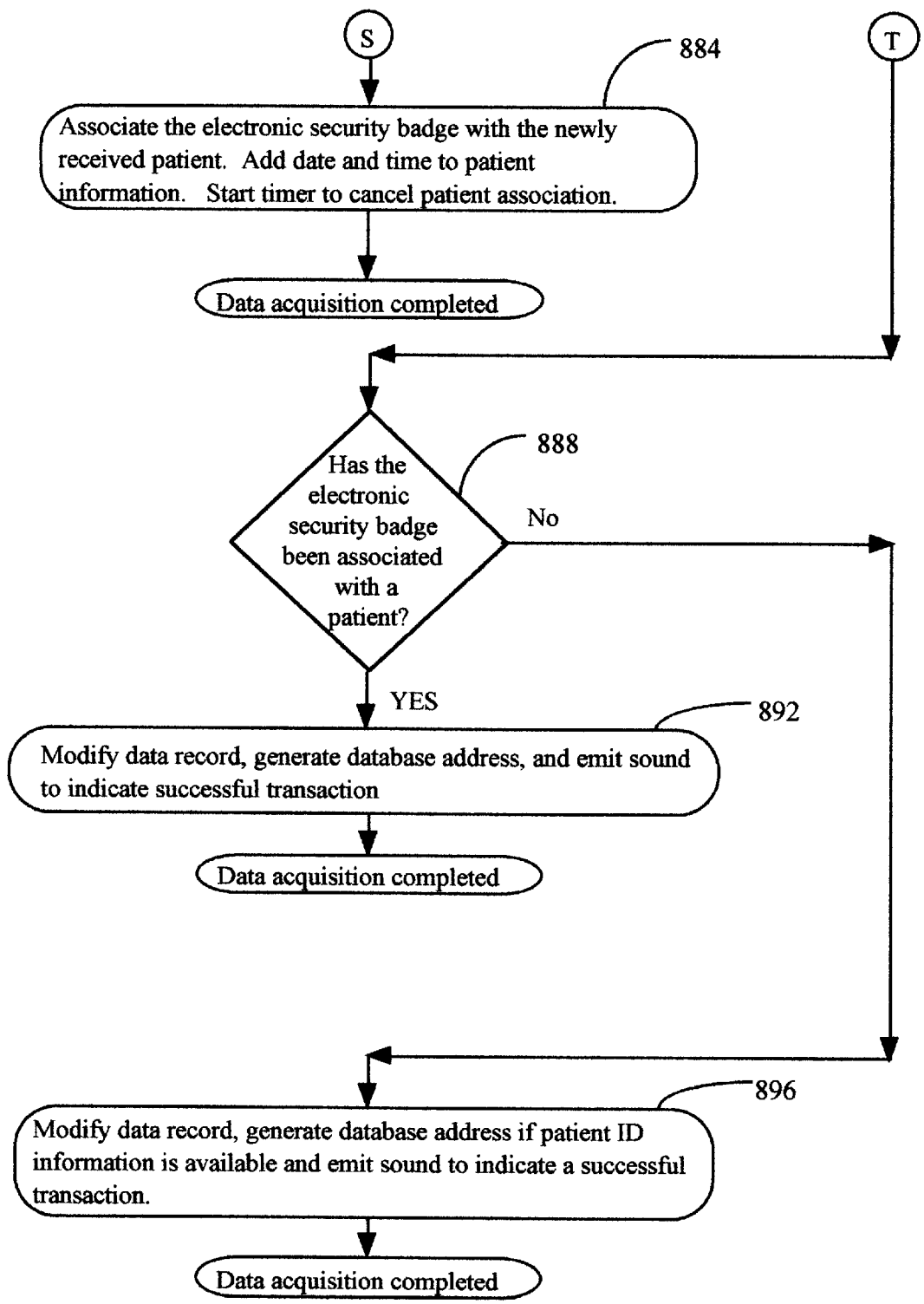

FIGS. 17A through 17C describe the operation of a security badge 10 in gathering and exchanging data with smart devices with which it is in communicable range. This operation is described particularly, but not by way of limitation, in the context of a hospital, where the exchange of information between a security badge 10 and a plurality of smart devices assigned to various patients and distributed throughout the hospital may be limited by the access privileges corresponding to patients whom or with whom the system user 68 is authorized to diagnose, treat, or interact. A single hospital room 104 (FIG. 4) may include a number of smart devices, including a computer terminal or workstation 80, a patient identification display 100, a bedside communication device 96, a patient treatment device 116, and a patient monitor 60, each of which may communicate with the security badge 10 or, in some circumstances, with each other.

In the preferred embodiment, data exchange between a security badge 10 and a smart device directed to a particular patient is conditioned upon and must be preceded by establishing an "association" between the system user 68 and the patient to whom the smart device is directed. Preferably, an association is digitally recorded by the security badge 10 in the form of information uniquely identifying the patient, the smart device and/or the security badge 10 itself, and the time and date of the association. This information may later be appended to data records exchanged with smart devices and computer terminals 60, providing the data records with a complete audit trail. Further, smart devices and security badges 10 themselves may also digitally record associations in a same or similar fashion.

Turning to step 824, a system user 68 attempts to initiate a communication link or exchange information with a smart device by depressing the activation button 18 (FIG. 1). Depending on the sophistication of these devices and the sensitivity of the information they contain, the communications established with these smart devices may or may not utilize public key cryptography. While link initialization may be automated rather than user-initiated, making the links user-initiated allows the security badge 10 to conserve energy and prevents unnecessary link initialization with devices about which the system user 68 is not concerned. The smart device preferably has compatible communication means with the security badge 10, both of which are preferably oriented in sufficient directional and spatial proximity to prevent other smart devices from also responding to signals transmitted by the security badge 10. Alternatively, the smart devices may be individually and manually enabled to communicate through the use of activation switches incorporated in the smart devices. Provided that the signal path between the security badge 10 and the smart device is substantially unobstructed and short enough that signal transmissions are not excessively attenuated, a communications link is established. In step 828, the security badge 10 evaluates the existence, if any, of an association between the security badge 10 and any patient (not necessarily the particular patient to which the linked smart device is directed). If there is no association, in step 832 the security badge 10 transmits to the smart device its own identification information and a request for data to be returned. If there is an association, in step 836 the security badge 10 transmits its own identification information, patient identification information (of the patient with whom the security badge 10 is associated), and a request for data to be returned. Steps 832 and 836 are each followed by step 840, in which the security badge 10 waits for a predetermined time period for a response from the smart device. If no response is received within the predetermined time period (step 848), then in step 852 the security badge 10 emits a first audible sound to alert the system user 68 that no response was received from the smart device, and in step 856 the operation initiated by the system user 68 in step 824 is terminated. If instead a response is received before the predetermined time period elapses (step 848), then in step 860 the data contained in the response signal is stored as a data record, and a timestamp is added to the data record.

If the data record recorded in step 860 is a patient identification record (step 864), and if the security badge 10 is already associated with that patient (step 868), then in step 876 the security badge 10 emits a second audible sound readily distinguishable to the human ear from the first audible sound of step 852, signaling to the system user 68 that the security badge 10 is associated with the patient and that the exchange of information was successful.

If the data record recorded in step 860 is a patient identification record (step 864), but the security badge 10 is not associated with any patient (steps 868 and 872), then in step 874 the security badge 10 records an association with the patient and in step 876 emits said second audible sound.

If the data record recorded in step 860 is a patient identification record (step 864), but the security badge 10 is associated with a second patient (steps 868 and 872), then in step 878 the association with said second patient is closed and a new association is established. In step 880 the security badge 10 emits said second audible sound twice to indicate the closure of a previous association and the initiation of the current association.

If the data record recorded in step 860 is not a patient identification record (step 864) but if the security badge 10 has been associated with a patient (step 888), then in step 892 the data record is modified to include staff and patient identification previously recorded in establishing the current association between security badge 10 and patient. The timestamp (recorded in step 860) and patient identification are further used to formulate a database address destination to store the data after it is transferred to the computer network 194 (FIG. 7). Further, the security badge 10 emits said second audible sound to indicate the successful transaction.

If the data record recorded in step 860 is not a patient identification record (step 864) and if the security badge 10 has not been associated with a patient (step 888), then in step 896 the data record is modified to include identification information attributable to the system user 68 (FIG. 3) to which the security badge 10 is assigned. If the data record includes patient information, it and the timestamp (recorded in step 860) are further used to formulate a database address destination to store the data after it is transferred to the computer network 194 (FIG. 7). Further, the security badge 10 emits said second audible sound to indicate the successful transaction.

Figure 9:
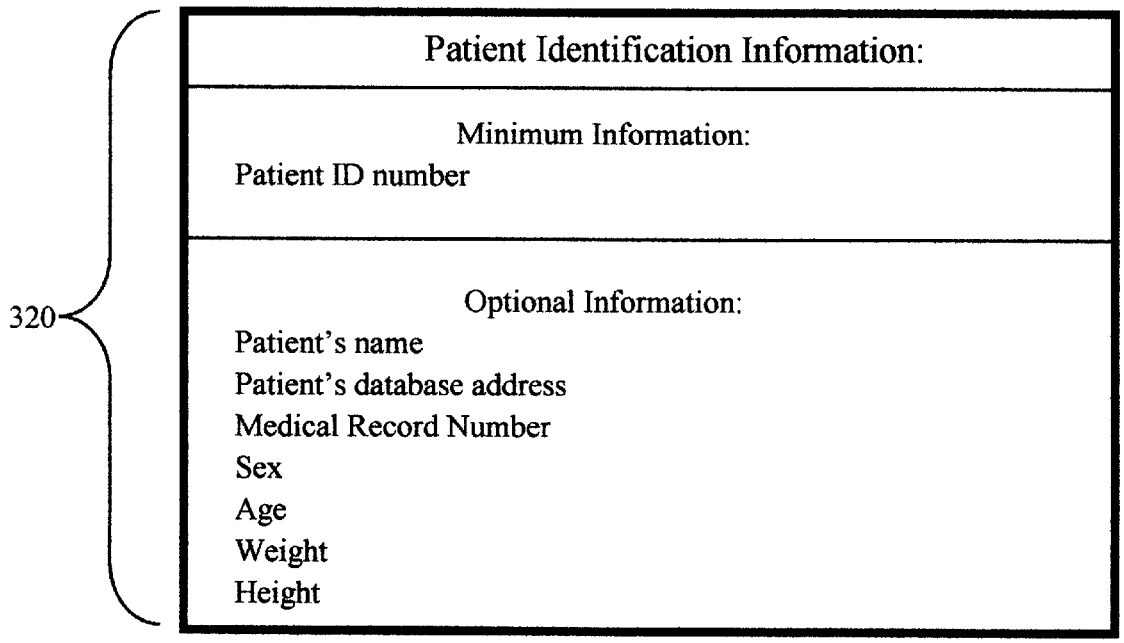
FIG. 9 presents the contents of the information transferred from a wrist bracelet according to the present invention to a security badge.

FIG. 9 illustrates the contents of the patient identification information 320 that may be transmitted by a wrist bracelet to a security badge 10 during a communications link with the security badge 10.

Although not illustrated by flow chart, an association with a patient may be is manually terminated by depressing activation button 18 for a few seconds, after which the security badge 10 emits an audible sound to indicate that the association has been terminated. An association with a patient may also be automatically terminated after a sufficient period of inactivity with respect to the security badge 10.

Figure 11:
FIG. 11 presents the contents of a digital message record incorporating a dictated message and other information corresponding to the dictated message.
Figure 18:
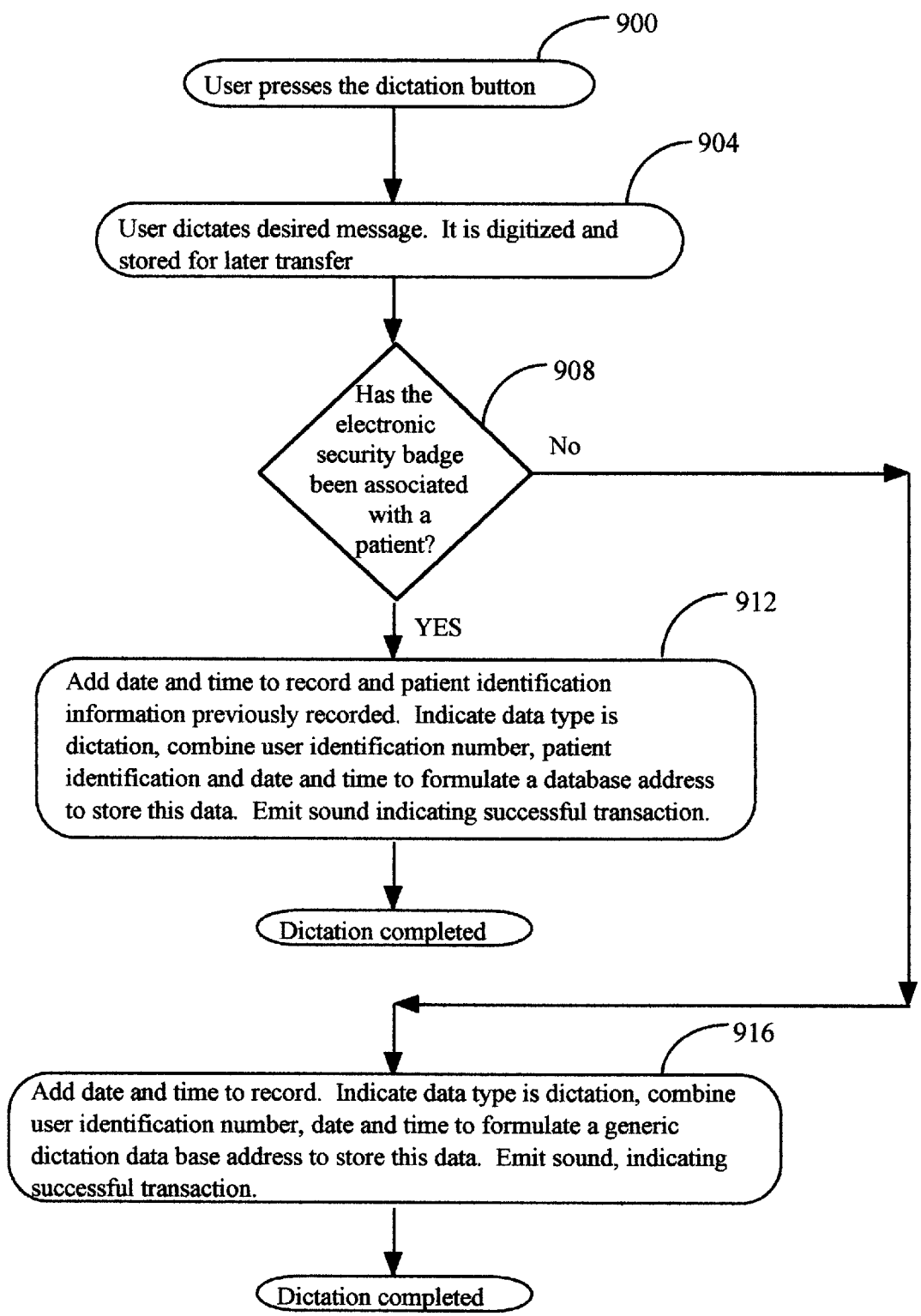
FIG. 18 is a function flow chart of the steps a security badge follows to record and generate addresses for dictated messages.

FIG. 18 describes the operation of the security badge 10 in digitally recording dictation. While observing or treating a patient, system user 68 may, in step 900, press the dictation button 26 (FIG. 1) and dictate messages (step 904) into the microphone 22 of the security badge 10. Digitizing circuitry incorporated in the processing circuitry 260 (FIG. 6) of the security badge 10 digitizes the message (step 904), which is recorded as a message record in memory element 262. If the security badge 10 is associated with a patient at the time the dictation is recorded (step 908), then in step 912 patient identification information and a timestamp are incorporated into the message record. Further, in step 912 a database address is formulated for the message record using the timestamp, the dictation data type, and patient identification information. Further, in step 912 the security badge 10 emits said second audible sound. If the security badge 10 is not associated with a patient at the time the dictation is recorded (step 908), then in step 916 a timestamp is incorporated into the message record. Further, in step 916 the dictation data type and timestamp are combined to form a partial database address for the message record. Further, in step 916 the security badge 10 emits said second audible sound. FIG. 11 illustrates the dictation information 360 that may be incorporated in the message record.

Other aspects, not included in FIGS. 17A through 17C, may be involved in communicating with or between certain smart devices. In one embodiment, the presence of a system user 68 in proximity to a patient enables communication between the patient's wrist bracelet 40 (FIG. 2) and the system user 68's security badge 10. The communication link may be initiated by depressing the activation button 18 on the security badge 10 and/or an activation button (not illustrated) on said wrist bracelet 40, provided there is a complete signal path between the security badge 10 and the wrist bracelet 40. Once a communication link is established, the security badge 10 identifies the patient and records the establishment of an association with that patient. The security badge 10 may also request and receive additional information stored by the wrist bracelet 40, providing a beep, vibration or other sensational signal to indicate a successful transmission or to alert the system user 68. The wrist bracelet 40 may also record in its own memory the staff identification information and current date and time from the security badge 10 to provide an audit trail of the caregivers who have associated themselves with the patien. If communication and association is established with another wrist bracelet 40 or, if not, after a preset period of time has elapsed, the security badge 10 regards the association to have terminated and alerts the system user 68 to this fact with another beep, vibration or other sensational means of communication.

In another embodiment, the wireless communication means 52 of wrist bracelet 40 (FIG. 2) may utilize alternate communication means, such as magnetic coupling or low power radio transmission, rather than the preferred infrared means of the security badge 10. Similarly, the bedside communication device 96 (FIG. 4) of a patient bed 88 may also utilize alternate communication means. Further, the communication range of wrist bracelets 40 or other smart devices may be limited in order to prevent two devices from receiving the same request. Instead of communicating directly with the security badge 10, the wrist bracelet 40 may communicate with patient identification display 100 directly or indirectly via communication with the communication means of a bedside communication device 96. A patient identification display 100 may also have transceiver device 64 compatible with the communication means 14 of the security badge 10. The smart devices may be arranged and implemented so that the patient identification display retrieves the patient identification information from the wrist bracelet 40 and electronically displays it. The patient identification display 100 may be programmed to cease displaying the patient identification information if the patient bedside device 96 no longer senses the presence of the patient. Patient chairs may be similarly equipped with smart devices to sense the presence of a patient and to convey such information to a patient identification display 100. Further, in order to establish an association with a patient, the security badge 10 may be required to establish a communication link with the patient identification display 100 instead of or in addition to the wrist bracelet 40, which patient identification display 100 would in turn transmit the patient identification information to the security badge 10. This would permit the transfer of patient identification information without the possible necessity of disrupting the patient in order to establish a communication link with the patient's wrist bracelet 40.

Figure 12:
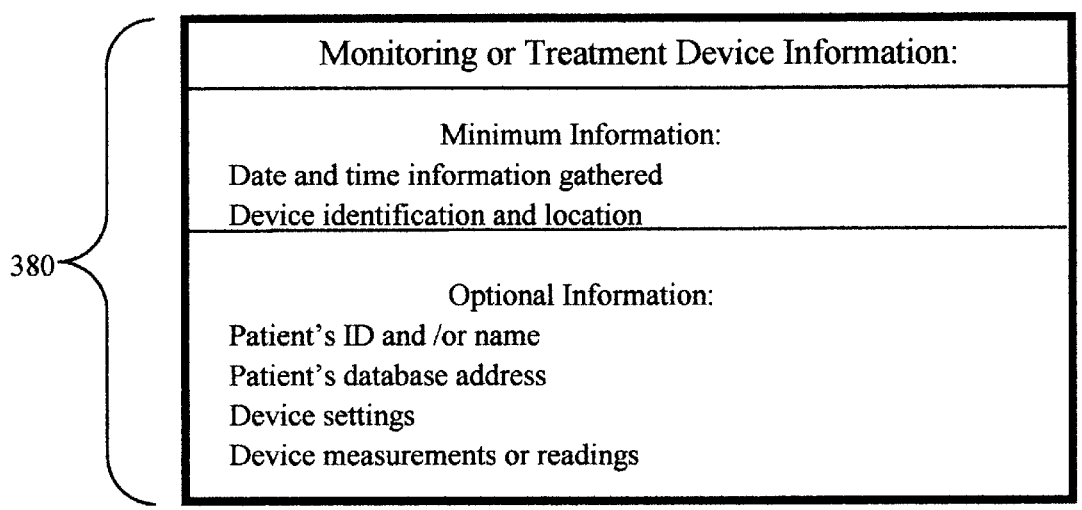
FIG. 12 is a list of information transferred from a patient monitoring or therapeutic device to a security badge.

If a new patient comes to occupy the patient room 104 or the patient bed 80, the patient identification display 100 would obtain the new patient identification information from the wrist bracelet 40 worn by the patient and may be structured to transmit that information to the Admit, Discharge and Transfer System 166 (FIG. 7) of the computer network 194. Alternatively, the patient identification display 100 could display a request for input indicating whether or not the new patient is to be marked as having been transferred to the instant patient room 104. A patient monitoring device 80 (FIG. 4) or bedside treatment device 178 (FIG. 7) may reject a data exchange request from a security badge 10 if the system user 68 wearing the security badge 10 is not authorized or cleared to diagnose or administer treatment to the patient. FIG. 12 illustrates the contents of the monitoring or treatment device information 380 that the bedside treatment device or patient monitoring device 80 may transmit to the security badge 10 if the data exchange is authorized. As part of a double-audit function, the monitoring device 80 or the bedside treatment device 178 would itself record any data transaction made with a security badge 10.

Figure 10:
FIG. 10 presents the contents of the information transferred from a medical container according to the present invention to a security badge.

The present invention also provides a medical container 200 (FIG. 5) equipped with an electronic identification device 224, programmable memory, and two-way communication means 212. In order for a system user 68 to administer medication to a patient, a hospital may make use of a medical container 200 (FIG. 5) according to the present invention, which limits access to the medication disposed within said medication container 200 upon the exchange of identification information between the system user 68's security badge 10 and the medical container 200. FIG. 10 illustrates the medication information 340 that a medical container 200 may transmit to a security badge 10 after access to the medication has been cleared. Preferably, both the security badge 10 and the medical container 200 store information, including time, staff and patient identification (collectively, "circumstances"), related to the transaction. Access to the medication disposed within the medical container 200 may be conditioned first upon the transfer and clearance of patient and staff identification from the security badge 10 to the medical container 200, in the form of a message generated by the security badge 10 indicative of the circumstances associated with the information or transaction. Receipt of such message and resulting verification of the transaction prevents medication from being inadvertently administered to the wrong patient. Access is provided by releasing the securing latch 232 of the medical container 200. The security badge 10 may also alert the system user 68 via an audible sound, vibration, or other sensational means to remind the system user 68 to administer the appropriate treatment. Means are also provided to permit the system user 68 to indicate that less than the entire amount of medication dispensed within the container 200 was administered. After the medication has been administered, the medical container 200 would preferably be returned to the pharmacy system 186 (FIG. 7), the unit dose medication dispenser 150, or to an appropriate workstation 154 or 155, where information relating to the administration of the medication, including the time, staff, and patient identification, would be transmitted to the computer network 194 for storage in a database 158 or 162.

D. System and Method for Dynamic Formatting and Address Generation of Data Records One aspect of the claimed invention provides that data records generated, recorded, and/or transmitted by the plurality of smart devices and security badges 10 be formatted and addressed according to uniform standards in order to minimize the need for human intervention in categorizing and archiving the hospital's many patient data records. Preferably, data records are formatted and addressed according to conventions, such as Java and the hyper text markup language (HTML), supporting interactive display by a multimedia display application such as a commercially available Internet browser or similar display, entry, and retrieval program using standardized formatting instructions. By formatting the data record in HTML format or as part of a Java applet or other display-compatible format, the receiving computer terminal or workstation will not need any additional programming or input to display or manipulate the data record. Preferably, formatting and addressing of data records received by the security badge 10 is done partially or entirely by the security badge 10 itself, using timestamps, patient identification, and the base contents 300 (FIG. 8) incorporated into the memory element 262 (FIG. 6) of the security badge 10. In this manner all the information required to handle the data record and to send it to an appropriate database is included in the data record transferred from the security badge 10.

FIGS. 13A through 13C and 14A through 14B illustrate data records relating to the dispensation and administration of medication.

Figure 13A:
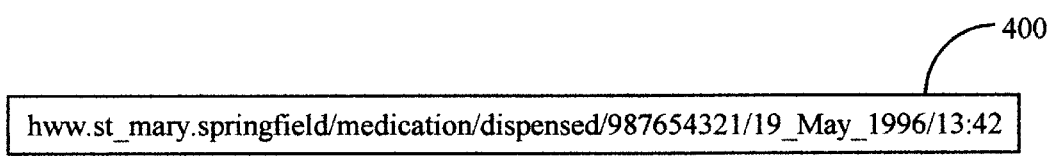
FIG. 13A is a textual representation of a URL address of medical dispensation record formed in part from the patient's identification number and a timestamp.

FIGS. 13A through 13C set forth a medication dispensation record 404 after it has been formatted according to HTML and uniform resource locator (URL) conventions. FIG. 13B illustrates the HTML codes incorporated into the medication dispensation record 404. FIG. 13C illustrates the medication dispensation record 404 as it is displayed by a browser 412, including hypertext links 416 and 420, respectively, to the patient's demographic record and the bibliographic record of the system user 68 who dispensed the medication. FIG. 13A illustrates the URL 400 generated for the medication dispensation record 404 which identifies the location at which it is or will be stored. Preferably, several data elements of a medication dispensation record 404 are stored by the medical container 200 as a medical information structure 340 (FIG. 10) when medicine is dispensed into the medical container 200. The medication dispensation record 404 is transmitted to a security badge 10 as part of a data exchange that takes place when a system user 68 administers the medicine disposed within the medical container 200.

FIGS. 14A through 14B illustrate the medication administration record 440, which is the medication dispensation record 404 (FIG. 13B) as modified by the security badge 10. FIG. 14A illustrates the HTML codes incorporated into the medication administration record 440. A security badge 10 that is associated with a patient will modify a medication dispensation record 404 that it receives from a medical container 200 (FIG. 5). Additions made to the medical administration record 440 include medication quantity fields 456 and 460 (FIG. 14A) indicating how much of the dispensed medicine was administered, provided that the system user 68 (FIG. 3) indicated that less than the full amount of medication dispensed was administered. Other additions include a report type field 448, a patient verification field 452, system user identification 464, and the date and time 468 access to the medical container 200 was provided, presumably indicating the time the medicine was administered. Hidden fields 472, incorporating information to be transmitted along with the record but concealed from view through the browser display, may also be added. Information appropriately concealed may include the initial quantities of medication dispensed, which information may be compared with the amount actually administered. Submit field 476 may be added to provide that contents of the hidden fields 472, including the entered medication quantities, may be transmitted for storage in a database 158 or 162 at the URL address indicated in the form field 444 of the medical administration record 440.

FIG. 14B illustrates the medication administration record 440 as it is displayed by a browser 480, including fields 492 and 496 indicating how much medicine was actually dispensed. When formatted data 440 is transmitted to a computer terminal 60, the security badge 10 may be programmed to emulate a file structure device, wherein the open file command of the browser 480 may be used to request data from the security badge 10.

The medical administration record 440 can be formatted as part of a Java applet and when transferred to a Java enabled computer terminal 60 can be displayed and modified without additional program codes.

While a particular embodiment of the invention has been illustrated and described, it will be obvious to those skilled in the art that various changes and modifications may be made without sacrificing the advantages provided by the principle of construction disclosed herein.

What is claimed is:

1. A method of initiating and maintaining access between a person having a mobile transceiver and data buffering device and an electronic system containing information and connected to a compatible transceiver device, said method comprising the steps of:

a. authenticating said mobile transceiver and data buffering device with said electronic system;

b. upon successful completion of said authenticating step, initiating access by one of at least said person and said mobile transceiver and data buffering device to said electronic system;

c. intermittently generating recommitment signals in said electronic system; and d. receiving said recommitment signal in said mobile transceiver and data buffering device and transmitting a recommitment response signal to said electronic system in response thereto, thereby maintaining access to said electronic system.

2. The method according to claim 1, further comprising the step of terminating access to said electronic system if said electronic system does not receive said recommitment response signal after one of at least a first preset time period and a first preset number of unanswered recommitment signals.

3. The method according to claim 1, further comprising the step of suspending access to said electronic system if said electronic system does not receive said recommitment response signal after one of at least a first preset time period and a first preset number of unanswered recommitment signals.

4. The method claim 3, wherein the step of suspending access to said electronic system is implemented by interrupting input to and output from a computer terminal in communication with said electronic system.

5. The method according to claim 3, further comprising the step of restoring access to said electronic system if said electronic system does receive said recommitment response signal after one of at least a first preset time period and a first preset number of unanswered recommitment signals but before one of at least a greater second preset time period and a greater second preset number of unanswered recommitment signals.

6. The method according to claim 5, further comprising the step of terminating access to said electronic system if said electronic system does not receive said recommitment response signal after one of at least said second preset time period and said second preset number of unanswered recommitment signals.

7. The method of claim 2 or claim 6, wherein said electronic system comprises a computer network including a computer terminal having temporary storage.

8. The method of claim 7, further comprising the step of conditioning access upon said person's entry of a password.

9. The method of claim 7, further comprising the steps of enlarging the connection between said computer terminal and said computer network when access is initiated and restricting the connection between said computer terminal and said computer network when access to said electronic system is terminated.

10. The method of claim 7, further comprising the step of removing any said information remaining in said temporary storage of said computer terminal provided that access to said computer network is terminated.

11. The method of claim 7, wherein said electronic system and said mobile transceiver and data buffering device employ public key cryptography.

12. The method of claim 7, further comprising the step of providing access through an interactive browser interface on said computer terminal.

13. A mobile transceiver and data buffering device for staff and data authentication and capable of sharing digital information with a compatible transceiver device, said transceiver and data buffering device comprising:

a. a processor;

b. means associated with said processor for receiving an interrogation signal transmitted over a wireless medium from said compatible transceiver device;

c. means associated with said processor for transmitting an authenticating response over a wireless medium to said compatible transceiver device, said authenticating response being responsive to said interrogation signal;

d. means associated with said processor for receiving intermittent recommitment signals generated by said said compatible transceiver device; and e. means associated with said processor for transmitting a recommitment response signal to said compatible transceiver device in response thereto, thereby maintaining access to said compatible transceiver device.

14. A controlled-access information system comprising:

a. a mobile transceiver and data buffering device for staff and data authentication, said transceiver and data buffering device comprising:

a processor;

means associated with said processor for receiving an interrogation signal transmitted over a wireless medium from a compatible transceiver device;

means associated with said processor for transmitting an authenticating response over a wireless medium to said compatible transceiver device, said authenticating response being responsive to said interrogation signal; means associated with said processor for receiving intermittent recommitment signals generated by said said compatible transceiver device; and means associated with said processor for transmitting a recommitment response signal to said compatible transceiver device in response thereto; and b. a compatible transceiver device connected to said information system and in communication with said mobile transceiver and data buffering device.

15. The controlled-access information system of claim 14, further comprising means for terminating access to said information system if said information system does not receive said recommitment response signal after one of at least a first preset time period and a first preset number of unanswered recommitment signals.

16. The controlled-access information system of claim 14, further comprising means for suspending access to said information system if said information system does not receive said recommitment response signal after one of at least a first preset time period and a first preset number of unanswered recommitment signals.

17. The controlled-access information system of claim 16, further comprising means for restoring access to said information system if said information system does receive said recommitment response signal after one of at least a first preset time period and a first preset number of unanswered recommitment signals but before one of at least a greater second preset time period and a greater second preset number of unanswered recommitment signals.

18. The controlled-access information system of claim 17, further comprising means for terminating access to said information system if said information system does not receive said recommitment response signal after one of at least said second preset time period and said second preset number of unanswered recommitment signals.

19. The controlled-access information system of claim 15 or claim 18, wherein said information system comprises a computer network including a computer terminal having a data storage device.

20. The controlled-access information system of claim 19, further comprising means for accepting entry of a password.

21. The controlled-access information system of claim 19, further comprising means for enlarging the connection between said computer terminal and said computer network when access is initiated and restricting the connection between said computer terminal and said computer network when access to said information system is terminated.

22. The controlled-access information system of claim 21, wherein said mobile transceiver and data buffering device weighs less than five kilograms and is substantially suitable for attachment to an article of apparel.

23. The controlled-access information system of claim 19, further comprising means in said mobile transceiver and data buffering device for digitally signing communications to be transmitted to said data storage device through said transmission means.

24. A mobile transceiver and data buffering device for staff and data authentication and communication with a plurality of smart devices, said mobile transceiver and data buffering device comprising:

a. means for identifying a wearer of said mobile transceiver and data buffering device;
   b. a memory for storing information;
   c. means for receiving information carried on a wireless medium for storage to said memory, whereby said plurality of smart devices may communicate with said mobile transceiver and data buffering device;
   d. means for transmitting information from said memory over a wireless medium, whereby said mobile transceiver and data buffering device may communicate with said plurality of smart devices;
   e. means for identifying a first smart device in proximity with said transceiver and data buffering device;
   f. means for automatically extracting information from said first smart device;
   g. means for transmitting said information to a data storage device with which said mobile transceiver and data buffering device is in proximity, whereby information contained in a smart device is uploaded substantially automatically to said mobile transceiver and data buffering device, and later downloaded to said data storage device.

25. The mobile transceiver and data buffering device of claim 24, wherein said plurality of smart devices comprise devices selected from the group consisting of computers, instruments, monitors, and treatment devices in a hospital.

26. The mobile transceiver and data buffering device of claim 24, wherein said data storage device comprises a computer terminal.

27. The mobile transceiver and data buffering device of claim 26, wherein said information is associated in said mobile transceiver and data buffering device with a circumstance selected from the group consisting of the date when said information was transmitted to said mobile transceiver and data buffering device, the time when said information was transmitted to said mobile transceiver and data buffering device, the identity of a patient with which said first smart device was associated, and the identity of said wearer of said mobile transceiver and data buffering device.

28. The mobile transceiver and data buffering device of claim 27, further comprising means for generating a message to said smart device indicative of the circumstance with which said information is associated.

29. The mobile transceiver and data buffering device of claim 26, further comprising:

means for alerting the wearer to impending receipt of information from said first smart device;
   means for permitting the wearer to indicate acceptance of said information from said first smart device.

30. The mobile transceiver and data buffering device of claim 29, further comprising means of digitally signing data records to be transmitted to said data storage device through said transmission means, whereby said data storage device is enabled to authenticate said mobile transceiver and data buffering device as the source of said information.

31. The mobile transceiver and data buffering device of claim 26, wherein said information is received from said first smart device by said transceiver and data buffering device and formatted for storage as a data record in a standardized format.

32. The mobile transceiver and data buffering device of claim 31, wherein said standardized format is the hypertext markup language.

* * * * *

UNITED STATES PATENT AND TRADEMARK OFFICE
CERTIFICATE OF CORRECTION

PATENT NO. : 5,960,085
DATED : September 28, 1999
INVENTOR(S) : Carlos de la Huerga It is certified that error appears in the above-identified patent and that said Letters Patent is hereby corrected as shown below:

At Col. 3, line 61, please delete "inlock" and substitute--unlock--therefor.

At Col. 10, line 40, before "device" insert-- components 14, an activation button 18, a microphone and analog-to-digital converter--.

Signed and Sealed this

Eighteenth Day of April, 2000

Attest:

Q. TODD DICKINSON

Attesting Officer

Director of Patents and Trademarks